(12) United States Patent
Tanabe et al.

(10) Patent No.: US 10,345,222 B2
(45) Date of Patent: Jul. 9, 2019

(54) ILLUMINATION DEVICE AND METHOD FOR GENERATING ILLUMINATION LIGHT

(71) Applicant: CITIZEN WATCH CO., LTD., Tokyo (JP)

(72) Inventors: Ayano Tanabe, Tokyo (JP); Nobuyuki Hashimoto, Saitama (JP); Tomomi Nemoto, Hokkaido (JP); Terumasa Hibi, Hokkaido (JP); Kohei Otomo, Hokkaido (JP); Yuichi Kozawa, Miyagi (JP)

(73) Assignee: CITIZEN WATCH CO., LTD., Tokyo (JP)

(*) Notice: Subject to any disclaimer, the term of this patent is extended or adjusted under 35 U.S.C. 154(b) by 0 days.

(21) Appl. No.: 16/076,377

(22) PCT Filed: Feb. 10, 2017

(86) PCT No.: PCT/JP2017/005002
§ 371 (c)(1),
(2) Date: Aug. 8, 2018

(87) PCT Pub. No.: WO2017/138655
PCT Pub. Date: Aug. 17, 2017

(65) Prior Publication Data
US 2019/0041316 A1 Feb. 7, 2019

(30) Foreign Application Priority Data
Feb. 10, 2016 (JP) ................... 2016-023924

(51) Int. Cl.
*G01J 4/00* (2006.01)
*G01N 21/01* (2006.01)
(Continued)

(52) U.S. Cl.
CPC ............. *G01N 21/01* (2013.01); *G02B 21/06* (2013.01); *G02B 27/09* (2013.01); *G02B 27/28* (2013.01); *G02F 1/13* (2013.01)

(58) Field of Classification Search
CPC ....... G01N 21/21; G01N 21/211; G01N 21/23; G01J 4/04; G01J 4/00
(Continued)

(56) References Cited

U.S. PATENT DOCUMENTS 6,042,234 A * 3/2000 Itoh ..................... G02B 27/283
348/E9.027
2006/0176542 A1* 8/2006 Muro ................. G01N 21/6458
359/290

FOREIGN PATENT DOCUMENTS

JP 2001-318231 A 11/2001
JP 2009-300486 A 12/2009
(Continued)

OTHER PUBLICATIONS

The International Bureau of WIPO, International Search Report for PCT patent application No. PCT/JP2017/005002, dated Apr. 11, 2017.
(Continued)

*Primary Examiner* — Md M Rahman

(57) ABSTRACT

An illumination device 11 has: a light source 1 for emitting polarized light having a Gaussian beam profile and including a first polarized light component and a second polarized light component orthogonal to each other; and a spiral phase element for imparting a phase modulation amount which increases for each predetermined step amount along a circumferential direction about an optical axis OA to the first polarized light component of transmitted polarized light from the light source 1 and making the beam profile of the first polarized light component a Laguerre-Gaussian beam profile, and forming a composite beam having a top-hat-
(Continued)

shaped beam profile in which the second polarized light component of the transmitted polarized light from the light source 1 and the first polarized light component having a Laguerre-Gaussian beam profile are synthesized.

11 Claims, 22 Drawing Sheets

(51) Int. Cl.
    *G02F 1/13*         (2006.01)
    *G02B 21/06*       (2006.01)
    *G02B 27/09*       (2006.01)
    *G02B 27/28*       (2006.01)

(58) Field of Classification Search
    USPC .......................................................... 356/364
    See application file for complete search history.

(56) References Cited

FOREIGN PATENT DOCUMENTS

| JP | 2011-126016 A | 6/2011 |
| JP | 2012-93675 A | 5/2012 |
| JP | 2013-104950 A | 5/2013 |

OTHER PUBLICATIONS

The International Bureau of WIPO, Written Opinion for PCT patent application No. PCT/JP2017/005002, dated Apr. 11, 2017.

* cited by examiner

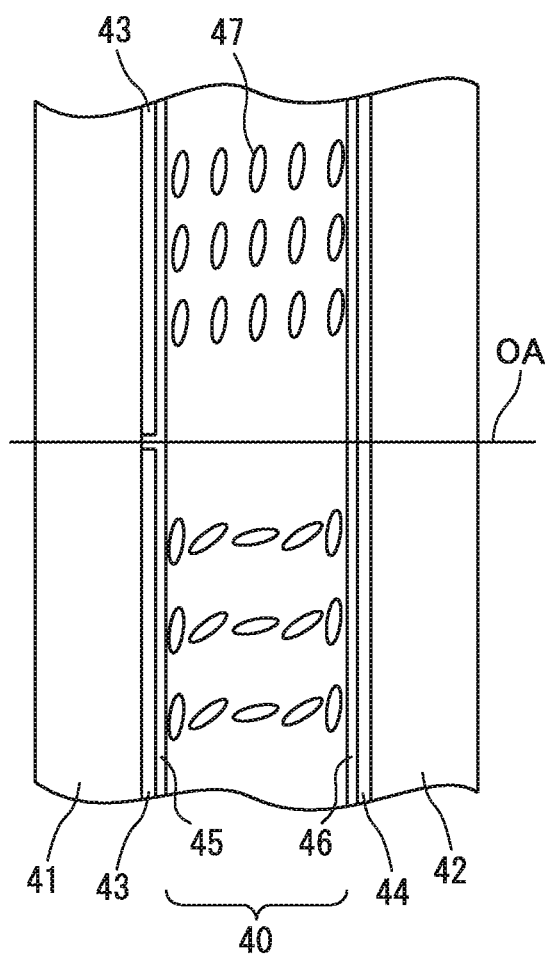

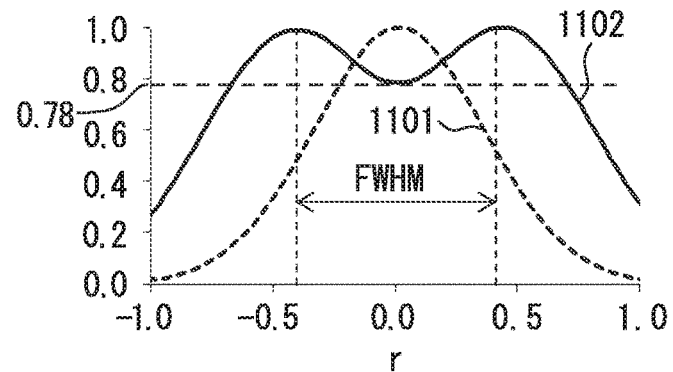
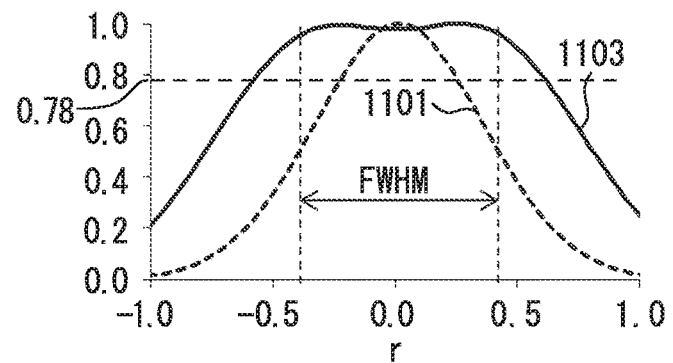
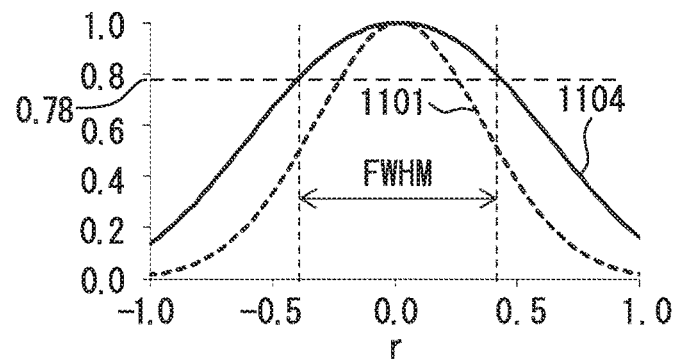

ILLUMINATION DEVICE AND METHOD FOR GENERATING ILLUMINATION LIGHT

FIELD

The present invention relates to an illumination device capable of providing beams having a certain beam profile, and to a method for generating illumination light used for such illumination device.

BACKGROUND

In recent years, beams having a so-called top-hat-shaped beam profile (hereinafter simply referred to as a top-hat beam for convenience of explanation) have been drawing attention. A top-hat beam has a beam profile in which the intensity is kept relatively high and uniform within a certain range from the beam center while the intensity is gradually decreased away from the border of the range. Since top-hat beams have a broader range of a substantially uniform energy distribution, application of top-hat beams to, for example, lighting in a spinning-disk confocal microscope or to laser machining devices has been studied.

An example of methods proposed for forming a top-hat beam includes forming a plurality of radiation patterns different in size by using a first optical member and then combining a smaller radiation pattern with a larger radiation pattern that is overlapped around the smaller pattern by using a second optical member (see Patent Literature 1, for example).

CITATION LIST

Patent Literature

Patent Literature 1: Japanese Unexamined Patent Publication (Kokai) No. 2011-126016

SUMMARY

Technical Problem

The aforementioned method needs individual optical paths corresponding to the respective radiation patterns to be formed, and thus restriction is imposed on a range where a top-hat beam can be generated. In other words, to form a top-hat beam at a desired radiation point, a position where the optical members used for forming the individual radiation patterns can be placed is limited. However, devices are not always allowed to have enough space for placing such optical members.

Therefore, an object of the present invention is to provide an illumination device that is capable of providing a top-hat beam and has greater flexibility in arrangement in an optical system.

Solution to Problem

According to one aspect of the present invention, an illumination device is provided. The illumination device includes:

a light source which emits polarized light that has a Gaussian beam profile and that includes a first polarized light component and a second polarized light component orthogonal to each other; and a spiral phase element which provides an amount of phase modulation to the first polarized light component of linearly polarized light passing through the spiral phase element on a plane orthogonal to an optical axis to turn the beam profile of the first polarized light component into a Laguerre-Gauss-like beam profile, where the amount of the phase modulation is increased by a predetermined amount along a circumference direction around the optical axis, and which forms a composite beam that has a top-hat-shaped beam profile and that is synthesized from the second polarized light component of the linearly polarized light passing through the spiral phase element and from the first polarized light component having the Laguerre-Gauss-like beam profile.

In the illumination device, it is preferable that the spiral phase element includes:

a liquid crystal layer which includes liquid crystal molecules aligned along the first direction;

a first transparent electrode which is disposed on one side of the liquid crystal layer along the optical axis; and a second transparent electrode which is disposed on another side of the liquid crystal layer along the optical axis, and which includes a plurality of partial electrodes arranged along the circumferential direction around the optical axis, wherein a voltage applied to a partial region of the liquid crystal layer between each of the plurality of the partial electrodes and the first transparent electrode is controlled such that the amount of phase modulation is increased by the predetermined amount between the partial regions adjacent to each other, whereby the beam profile of the first polarized light component is turned into the Laguerre-Gauss-like beam profile. Preferably, the polarized light coming from the light source is linearly polarized light which has a polarization plane forming a predetermined angle greater than 0° and less than 90° with the first direction, the first polarized light component is a component parallel to the first direction, and the second polarized component is a component orthogonal to the first direction.

In this case, it is preferable that the predetermined angle is within an angular range in which the composite beam has an intensity of at least 0.8 times a maximum intensity of the composite beam within a range of a full width at half maximum of the second polarized light component.

Preferably, the illumination device further includes:

a support unit which supports either one of the spiral phase element and the light source rotatably around the optical axis;

a memory which stores a table representing a correspondence relationship between a distance from the spiral phase element to a plane irradiated with the composite beam and an angle formed between a polarization plane of the polarized light and the first direction; and a controller which refers to the table and controls the support unit so as to rotate the either one of the spiral phase element and the light source so that an angle formed between the polarization plane of the polarized light coming from the light source and the first direction corresponds to the distance from the spiral phase element to the irradiated plane.

Preferably, the illumination device further includes:

a memory which stores first voltages to be applied between the plurality of the individual partial electrodes and the first transparent electrode when phase modulation provided by the spiral phase element to the first polarized light component over one cycle of turning along the circumference direction is increased by an amount equivalent to a wavelength of the polarized light coming from the light source, and which stores second voltages to be applied between the plurality of the individual partial electrodes and the first transparent electrode when phase modulation provided by the spiral phase element to the first polarized light component over one cycle of turning along the circumference direction is increased by an amount equivalent to twice the wavelength of the polarized light coming from the light source; and a controller which sets a voltage to be applied between each of the plurality of the partial electrodes and the first transparent electrode in accordance with the first voltages when phase modulation provided by the spiral phase element to the first polarized light component is increased over one cycle of turning along the circumference direction by an amount equivalent to the wavelength of the polarized light coming from the light source, and which sets a voltage to be applied between each of the plurality of the partial electrodes and the first transparent electrode in accordance with the second voltages when phase modulation provided by the spiral phase element to the first polarized light component is increased over one cycle of turning along the circumference direction by an amount equivalent to twice the wavelength of the polarized light coming from the light source.

In this case, the illumination device preferably further includes a support unit which supports either one of the spiral phase element and the light source rotatably around the optical axis, and preferably, the memory further stores a first angle to be formed between the polarization plane of the polarized light and the first direction when phase modulation provided by the spiral phase element to the first polarized light component over one cycle of turning along the circumference direction is increased by an amount equivalent to the wavelength of the polarized light coming from the light source, and further stores a second angle to be formed between the polarization plane of the polarized light and the first direction when phase modulation provided by the spiral phase element to the first polarized light component over one cycle of turning along the circumference direction is increased by an amount equivalent to twice the wavelength of the polarized light coming from the light source, and the controller causes the support unit to rotate either one of the spiral phase element and the light source so that the predetermined angle is equal to the first angle when phase modulation provided by the spiral phase element to the first polarized light component over one cycle of turning along the circumference direction is increased by an amount equivalent to the wavelength of the polarized light, and causes the support unit to rotate either one of the spiral phase element and the light source so that the predetermined angle is equal to the second angle when phase modulation provided by the spiral phase element to the first polarized light component over one cycle of turning along the circumference direction is increased by an amount equivalent to twice the wavelength of the polarized light.

Preferably, in the illumination device, the polarized light coming from the light source is circularly polarized light or elliptically polarized light.

In this case, the spiral phase element preferably includes:

a liquid crystal layer which includes liquid crystal molecules aligned along a first direction that is parallel to the first polarized light component;

a first transparent electrode which is disposed on one side of the liquid crystal layer along the optical axis; and a second transparent electrode which is disposed on another side of the liquid crystal layer along the optical axis, and which includes a plurality of partial electrodes arranged along the circumferential direction around the optical axis, wherein a voltage applied to a partial region of the liquid crystal layer between each of the plurality of the partial electrodes and the first transparent electrode is preferably controlled such that the amount of phase modulation is increased by the predetermined amount between the partial regions adjacent to each other, whereby the beam profile of the first polarized light component is turned into a Laguerre-Gauss-like beam profile.

Preferably, the polarized light is elliptically polarized light and the illumination device includes:

a support unit which supports either one of the spiral phase element and the light source rotatably around the optical axis;

a memory which stores a table representing a correspondence relationship between a distance from the spiral phase element to a plane irradiated with the composite beam and an angle formed between a major axis of the polarized light and the first direction; and a controller which refers to the table and controls the support unit so as to rotate the either one of the spiral phase element and the light source so that an angle formed between the major axis of the polarized light coming from the light source and the first direction corresponds to the distance from the spiral phase element to the plane irradiated with the composite beam.

According to another aspect of the present invention, a method for generating illumination light in an illumination device is provided, the illumination device including:

a light source which emits illumination light that has a Gaussian beam profile, that is linearly polarized light or elliptically polarized light, and that has a predetermined polarization plane;

a spiral phase element which provides an amount of phase modulation on a plane orthogonal to the optical axis, the amount being increased by a predetermined amount along a circumference around an optical axis, to a first polarized light component of the illumination light passing through the spiral phase element, the first polarized light component having a first direction on a plane orthogonal to the optical axis, to turn the beam profile of the first polarized light component into a Laguerre-Gauss-like beam profile, and which forms a composite beam that has a top-hat-shaped beam profile and that is synthesized from a second polarized light component of the illumination light passing through the spiral phase element, the second polarized light component being orthogonal to the first polarized light component, and from the first polarized light component having the Laguerre-Gauss-like beam profile, wherein the spiral phase element includes:

a liquid crystal layer which includes liquid crystal molecules aligned along the first direction;

a first transparent electrode which is disposed on one side of the liquid crystal layer along the optical axis; and a second transparent electrode which is disposed on another side of the liquid crystal layer along the optical axis, and which includes a plurality of partial electrodes arranged along the circumferential direction around the optical axis.

The method for generating illumination light includes the steps of:

applying a voltage to a partial region of the liquid crystal layer between each of the plurality of the partial electrodes and the first transparent electrode so that the amount of phase modulation is increased by the predetermined amount between the partial regions adjacent to each other to turn the beam profile of the first component into a Laguerre-Gauss-like beam profile; and referring to a table representing a correspondence relationship between a distance from the spiral phase element to a plane irradiated with the composite beam and an angle formed between the predetermined polarization plane and the first direction, to rotate either one of the light source and the spiral phase element around the optical axis so that an angle formed between the predetermined polarization plane and the first direction corresponds to the distance.

According to still another aspect of the present invention, a method for generating illumination light in an illumination device is provided, wherein the light device includes:

a light source which emits polarized light that has a Gaussian beam profile and that includes a first polarized light component and a second polarized light component orthogonal to each other; and a spiral phase element which provides an amount of phase modulation to the first polarized light component of the polarized light coming from the light source and passing through the spiral phase element to turn the beam profile of the first polarized light component into a Laguerre-Gauss-like beam profile, where the amount of the phase modulation is increased by a predetermined amount along a circumference direction around an optical axis, and which forms a composite beam that has a top-hat-shaped beam profile and that is synthesized from the second polarized light component of the polarized light coming from the light source and passing through the spiral phase element and from the first polarized light component having the Laguerre-Gauss-like beam profile, wherein the spiral phase element includes:

a liquid crystal layer which includes liquid crystal molecules aligned along a first direction that is parallel to the first polarized light component;

a first transparent electrode which is disposed on one side of the liquid crystal layer along the optical axis; and a second transparent electrode which is disposed on another side of the liquid crystal layer along the optical axis, and which includes a plurality of partial electrodes arranged along the circumferential direction around the optical axis.

The method for generating illumination light includes the steps of:

setting a voltage to be applied between each of the plurality of the partial electrodes and the first transparent electrode in accordance with first voltages when phase modulation provided by the spiral phase element to the first polarized light component is increased over one cycle of turning along the circumference direction by an amount equivalent to a wavelength of the polarized light coming from the light source, while setting a voltage to be applied between each of the plurality of the partial electrodes and the first transparent electrode in accordance with second voltages when phase modulation provided by the spiral phase element to the first polarized light component is increased over one cycle of turning along the circumference direction by an amount equivalent to twice the wavelength of the polarized light coming from the light source; and applying the set voltage to a partial region of the liquid crystal layer between each of the plurality of the partial electrodes and the first transparent electrode to turn the beam profile of the first polarized light component into a Laguerre-Gauss-like beam profile.

Advantageous Effects of Invention

The illumination device according to the present invention can provide a top-hat beam and have greater flexibility in arrangement in an optical system.

BRIEF DESCRIPTION OF DRAWINGS

FIG. 2C is a partial enlarged view of FIG. 2B;

FIG. 11A illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the propagation distance from the VORTEX liquid crystal element to the observation plane is equal to the Rayleigh length, and the angle θ formed between the alignment direction of liquid crystal molecules in the VORTEX liquid crystal element and the polarization direction of the Gauss beam emitted by the light source is 28°.

FIG. 11B illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the propagation distance from the VORTEX liquid crystal element to the observation plane is equal to the Rayleigh length, and the angle θ formed between the alignment direction of liquid crystal molecules in the VORTEX liquid crystal element and the polarization direction of the Gauss beam emitted by the light source is 34°.

FIG. 11C illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the propagation distance from the VORTEX liquid crystal element to the observation plane is equal to the Rayleigh length, and the angle θ formed between the alignment direction of liquid crystal molecules in the VORTEX liquid crystal element and the polarization direction of the Gauss beam emitted by the light source is 41°.

DESCRIPTION OF EMBODIMENTS

An illumination device according to one embodiment will be described with reference to the drawings. The illumination device includes: a light source emitting polarized light that has a Gaussian beam profile and that includes a first polarized light component and a second polarized light component orthogonal to each other; and a VORTEX liquid crystal element capable of increasing phase modulation by a predetermined amount along a circumferential direction around an optical axis. The VORTEX liquid crystal element and the light source are placed such that a certain angle greater than 0° and less than 90° is formed between the polarization plane of either the first polarized light component or the second polarized component emitted by the light source and the alignment direction of the VORTEX liquid crystal element. As a result, a modulation component and a non-modulation component are created, where the modulation component has a Laguerre-Gauss-like beam profile generated by passing the linearly polarized light through the VORTEX liquid crystal element, and the non-modulation component has a Gaussian beam profile with no phase modulation given by the VORTEX liquid crystal element. A top-hat beam is then created by synthesizing from the modulation component and the non-modulation component. Because each of the beam profiles of the modulation and non-modulation components is one of beam propagation modes, the beam profiles are maintained throughout an illumination optical system. Therefore, the illumination device can provide a top-hat beam even though where the VORTEX liquid crystal element is placed at any desired position in the illumination optical system.

For convenience of description, a beam having a Gaussian beam profile is hereinafter simply referred to as a Gauss beam, while a beam having a Laguerre-Gauss-like beam profile is hereinafter referred to as a Laguerre-Gauss-like beam.

Figure 1:
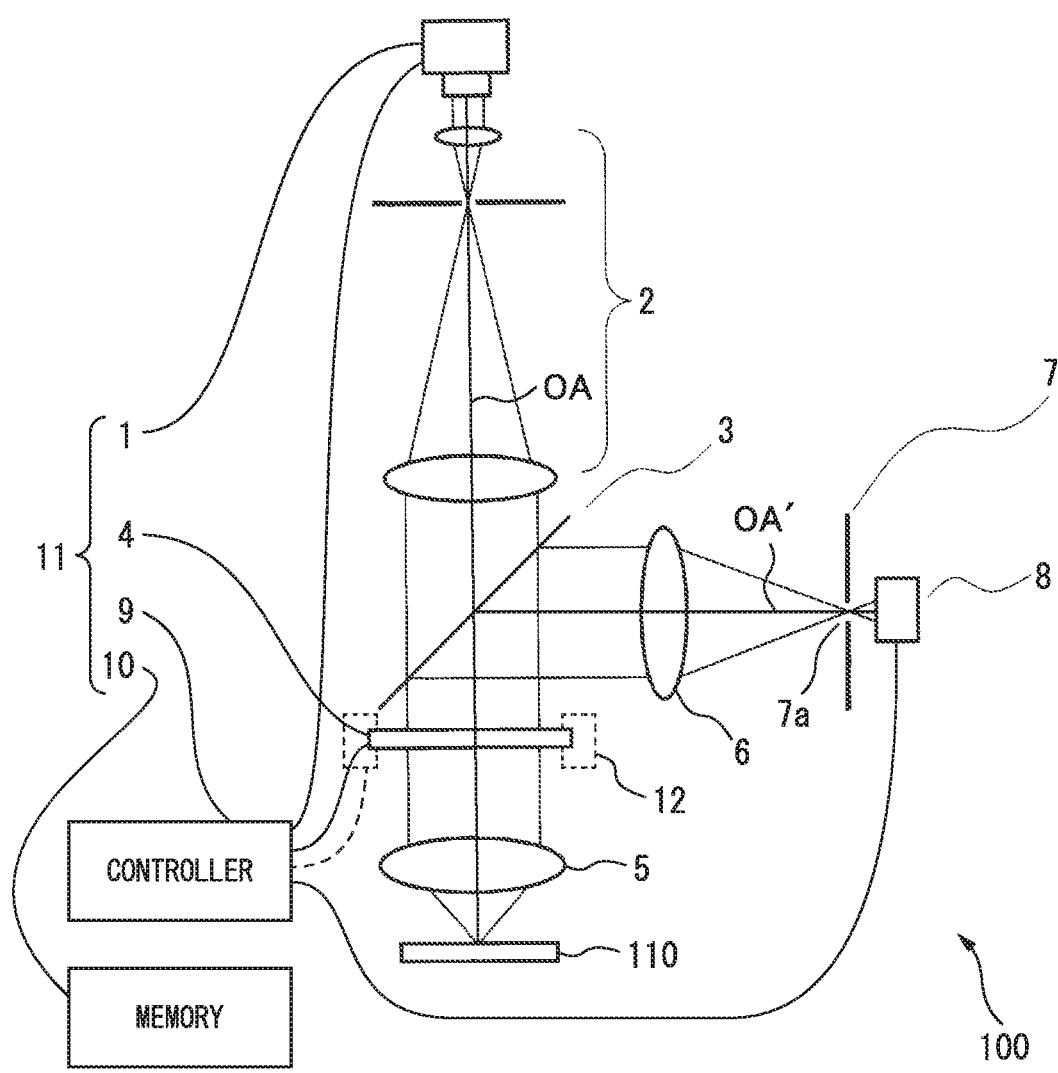
FIG. 1 is a schematic configuration diagram of a microscope device that includes an illumination device according to one embodiment of the present invention.

FIG. 1 is a schematic configuration diagram of a microscope device that includes an illumination device according to one embodiment of the present invention. As illustrated in FIG. 1, the microscope device 100 includes a light source 1, a collimate optical system 2, a beam splitter 3, a VORTEX liquid crystal element 4, an objective lens 5, a confocal optical system 6, a mask plate 7, a light receiving element 8, a controller 9, and a memory 10. Among these elements, the light source 1, the VORTEX liquid crystal element 4, the controller 9, and the memory 10 are included in the illumination device 11.

The microscope device 100 may include, on an optical path, any of various correction optical systems such as a spherical aberration correction optical system.

The light source 1 emits illumination light that has a Gaussian beam profile and that has polarized light including a first polarized light component and a second polarized light component orthogonal to each other. For this purpose, the light source 1 may include, for example, a semiconductor laser that emits linearly polarized light having a certain polarization plane. Alternatively, the light source 1 may include a gas laser such as an argon-ion laser or a solid-state laser such as a YAG laser.

In addition, the light source 1 may include a plurality of light emitting elements that emit light beams of different wavelengths falling within a certain wavelength region such as, for example, from 351 to 750 nm. In this case, the light source 1 causes any one of the light emitting elements to emit illumination light in accordance with a control signal from the controller 9.

The collimate optical system 2 is placed between the light source 1 and the beam splitter 3 so that the light source 1 is positioned at the front focal point of the collimate optical system 2. The collimate optical system 2 turns the illumination light emitted from the light source 1 into parallel beam of light. The parallel beam of illumination light is directed toward the beam splitter 3.

The beam splitter 3 is placed between the collimate optical system 2 and the VORTEX liquid crystal element 4. The illumination light beam incident from the collimate optical system 2 travel straight through the beam splitter 3 toward the VORTEX liquid crystal element 4. The beam splitter 3 causes part of the light reflected or scattered by the sample 110 or part of the fluorescent light emitted by the sample 110 to be reflected and directed toward the confocal optical system 6.

The VORTEX liquid crystal element 4, which is an example of spiral phase elements, is placed, for example, between the beam splitter 3 and the objective lens 5 such that its center coincides with the optical axis OA that is defined by the collimate optical system 2 and the objective lens 5. When the illumination light passes through the VORTEX liquid crystal element 4, the VORTEX liquid crystal element 4 generates a modulation component that has a Laguerre-Gauss-like beam profile, and generates a top-hat beam, which is a composite beam synthesized from a non-modulation component and the modulation component.

The VORTEX liquid crystal element 4 will be described in detail later.

In the present embodiment, the VORTEX liquid crystal element 4 is placed between the beam splitter 3 and the objective lens 5. However, the VORTEX liquid crystal element 4 may be placed at some other position. For example, the VORTEX liquid crystal element 4 may be placed between the light source 1 and the collimate optical system 2, or inside the collimate optical system 2, or between the collimate optical system 2 and the beam splitter 3.

The objective lens 5 focuses the top-hat beam outgoing from the VORTEX liquid crystal element 4 on an observation plane defined on or in the sample 110. The light reflected or scattered by the observation plane or the fluorescent light emitted from the observation plane passes through the objective lens 5 again to be turned into a parallel light beam. The light beam passes through the VORTEX liquid crystal element 4 to enter the beam splitter 3, and part of the light beam is reflected and directed toward the confocal optical system 6.

The confocal optical system 6 focuses the incident light beam on the focal plane. The mask plate 7 is placed near the focal plane of the confocal optical system 6, between the confocal optical system 6 and the light receiving element 8. On the mask plate 7, a confocal pinhole 7a is made along the optical axis that is defined by the objective lens 5 and the confocal optical system 6. In this way, the light reflected or scattered near the focal point of the objective lens 5 or the fluorescent light emitted near the focal point enters the confocal optical system 6 in the form of a parallel beam, which is then focused by the confocal optical system 6 on a point near the confocal pinhole 7a, thus allowed to pass through the confocal pinhole 7a to reach the light receiving element 8. In contrast, a light beam coming from a position out of the focal point of the objective lens 5 is focused on a position out of the confocal pinhole 7a to be masked by the mask plate 7, thus failing to reach the light receiving element 8. As a result, the microscope device 100 can obtain a high-contrast image of the sample 110.

The microscope device 100 may be a spinning confocal microscope. In this case, the mask plate may be disposed between, for example, the VORTEX liquid crystal element 4 and the objective lens 5 and may be rotatably supported with a plurality of pinholes made therein.

The light receiving element 8 includes, for example, semiconductor light receiving elements such as a plurality of CCDs or C-MOS arranged in an array. Each individual semiconductor light receiving element outputs an electrical signal corresponding to the intensity of a received light. The light receiving element 8 then calculates an average of the electrical signals output by the individual semiconductor light receiving elements, and outputs to the controller 9 an electrical signal corresponding to the average value, as a light intensity signal representing the intensity of the received light. Alternatively, the light receiving element 8 may include a photomultiplier tube. In this case, the light receiving element 8 generates an electrical signal corresponding to the intensity of the light received and multiplied by the photomultiplier, and outputs to the controller 9 the electrical signal as a light intensity signal representing the intensity of the received light.

The controller 9 includes, for example, one or more processors and an interface circuit used for connecting the controller 9 to the individual elements of the microscope device 100. The controller 9 controls the light source 1 and the VORTEX liquid crystal element 4. The controller 9 supplies a certain amount of electric power to the light source 1 to cause the light source 1 to output illumination light. When the light source 1 includes a plurality of light emitting elements, the controller 9 sends the light source 1 a control signal indicating that any one of the light emitting elements is to emit illumination light in accordance with, for example, a user operation performed through a user interface.

In addition, the controller 9 creates an image of the observation plane defined on or in the sample 110, on the basis of a light intensity signal received from the light receiving element 8. For this purpose, for example, a galvano mirror is placed on an optical path of the illumination light so that a plurality of measurement points equally spaced on the observation plane in two dimensions are each positioned at an illumination light spot. While rotating the galvano mirror, the controller 9 receives light intensity signals corresponding to the individual measurement points from the light receiving element 8. The controller 9 can obtain a two-dimensional image of the observation plane on the sample 110 by, for example, generating the image using each of the light intensity signals of the individual measurement points as a single pixel value.

Furthermore, the controller 9 includes a drive circuit, through which the controller 9 adjusts the voltage applied to the VORTEX liquid crystal element 4, thus controlling the VORTEX liquid crystal element 4 so as to form a top-hat beam.

For this purpose, the controller 9 controls the drive circuit so that the voltage corresponding to the wavelength of a light beam output by the light source 1 is applied to the liquid crystal layer in the VORTEX liquid crystal element 4.

In particular, when the light source 1 includes a plurality of light emitting elements that emit light beams of different wavelengths, the controller 9 adjusts the voltage applied to the liquid crystal layer in the VORTEX liquid crystal element 4, depending on which light emitting element is caused to emit a light beam.

The drive voltage applied by the drive circuit to the liquid crystal layer included in the VORTEX liquid crystal element 4 may be an alternating voltage generated through pulse-height modulation (PHM) or pulse-width modulation (PWM). In addition, the drive circuit may use overdrive to drive the individual liquid crystal elements included in the VORTEX liquid crystal element 4 so as to accelerate responses from the liquid crystal elements.

The memory 10 includes, for example, a volatile readable and writable semiconductor memory circuit or a nonvolatile read-only memory circuit. The memory 10 may further include a magnetic or optical recording medium and a device for accessing the medium. The memory 10 is connected to the controller 9 and stores data to be used by the controller 9 for controlling the light source 1 and the VORTEX liquid crystal element 4. The memory 10 may further store a two-dimensional image of the sample 110 on the observation plane, as generated by the controller 9.

The following describes the VORTEX liquid crystal element 4 in detail.

Figure 2A:
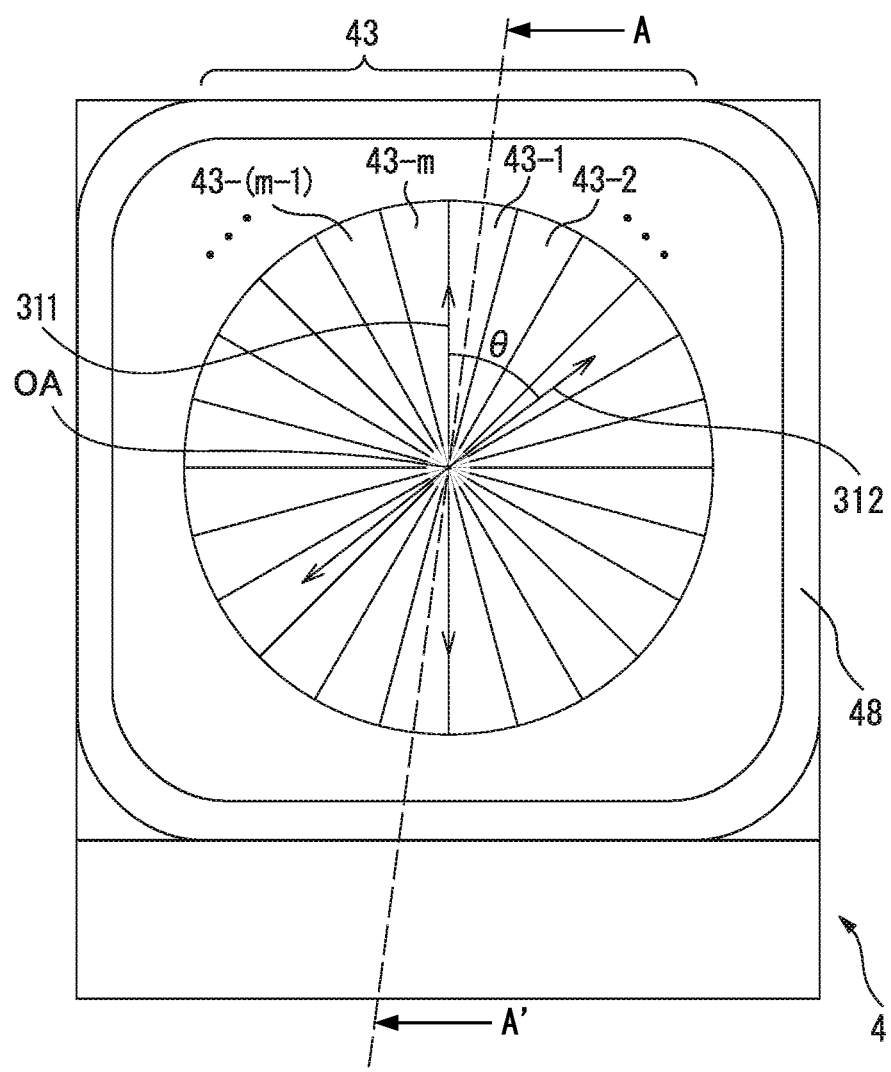
FIG. 2A is a schematic front view of a VORTEX liquid crystal element.
Figure 2B:
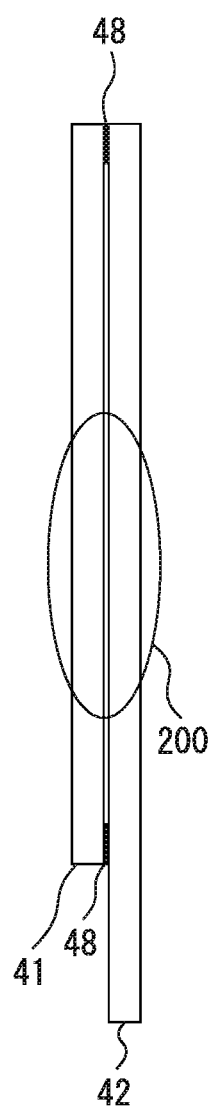
FIG. 2B is a schematic cross-sectional side view of the VORTEX liquid crystal element taken along the line indicated by arrows A and A' in FIG. 2A.

FIG. 2A is a schematic front view of the VORTEX liquid crystal element 4. FIG. 2B is a schematic cross-sectional side view of the VORTEX liquid crystal element 4 taken along the line indicated by arrows A and A' in FIG. 2A. FIG. 2C is a partial enlarged view of a portion 200 illustrated in FIG. 2B.

The VORTEX liquid crystal element 4 includes a liquid crystal layer 40 and transparent substrates 41 and 42 disposed on both sides of the liquid crystal layer 40 along the optical axis OA, the transparent substrates 41 and 42 being substantially in parallel with each other. The VORTEX liquid crystal element 4 further includes a transparent electrode 43 disposed between the transparent substrate 41 and the liquid crystal layer 40, and a transparent electrode 44 disposed between the liquid crystal layer 40 and the transparent substrate 42. Liquid crystal molecules 47 in the liquid crystal layer 40 are contained in the space surrounded by the transparent substrates 41 and 42 and a sealing member 48. The liquid crystal layer 40 has a thickness of 20 to 30 μm, for example, which is adequate enough for the VORTEX liquid crystal element 4 to provide a certain amount of phase modulation to the illumination light passing through the VORTEX liquid crystal element 4.

The transparent substrates 41 and 42 are made of a material transparent to the illumination light emitted by the light source 1, such as glass or resin. The transparent electrodes 43 and 44 are made of, for example, a material referred to as ITO, which is made by adding tin oxide to indium oxide. An alignment film 45 is disposed between the transparent electrode 43 and the liquid crystal layer 40. Likewise, an alignment film 46 is disposed between the transparent electrode 44 and the liquid crystal layer 40. The alignment films 45 and 46 align the liquid crystal molecules 47 along a certain direction.

The liquid crystal molecules 47 contained in the liquid crystal layer 40 are, for example, homogeneously aligned. As indicated by an arrow 311, the liquid crystal molecules 47 are aligned along the alignment direction that forms a certain angle θ greater than 0° and less than 90° with a polarization plane 312 of the incident illumination light. The alignment direction is an example of a first direction. The range of the angle θ will be described later.

In the present embodiment, the transparent electrode 43 includes a plurality of fan-shaped partial electrodes 43-1 to 43-$m$ equally segmented along the circumferential direction around the optical axis OA, where m is an integer equal to or greater than 2. In the present embodiment, the transparent electrode 43 includes 24 partial electrodes. However, the number of partial electrodes is not limited to 24, and thus may be 16 or 32, for example. The partial electrodes 43-1 to 43-$m$ entirely cover an active region where the liquid crystal molecules 47 are to be driven. In contrast, the transparent electrode 44 may be formed as a single transparent electrode entirely covering the active region. In FIG. 2A, a gap between partial electrodes is indicated by a solid line.

The controller 9 adjusts the voltage applied between the individual partial electrodes 43-1 to 43-$m$ and the transparent electrode 44 opposed thereto across the liquid crystal layer 40. As a result, the VORTEX liquid crystal element 4 provides an amount of phase modulation to a component, which is parallel to the alignment direction, of the linearly polarized light passing through the liquid crystal layer 40, where the amount of phase modulation gradually increases along the circumferential direction around the optical axis OA.

Figure 3:
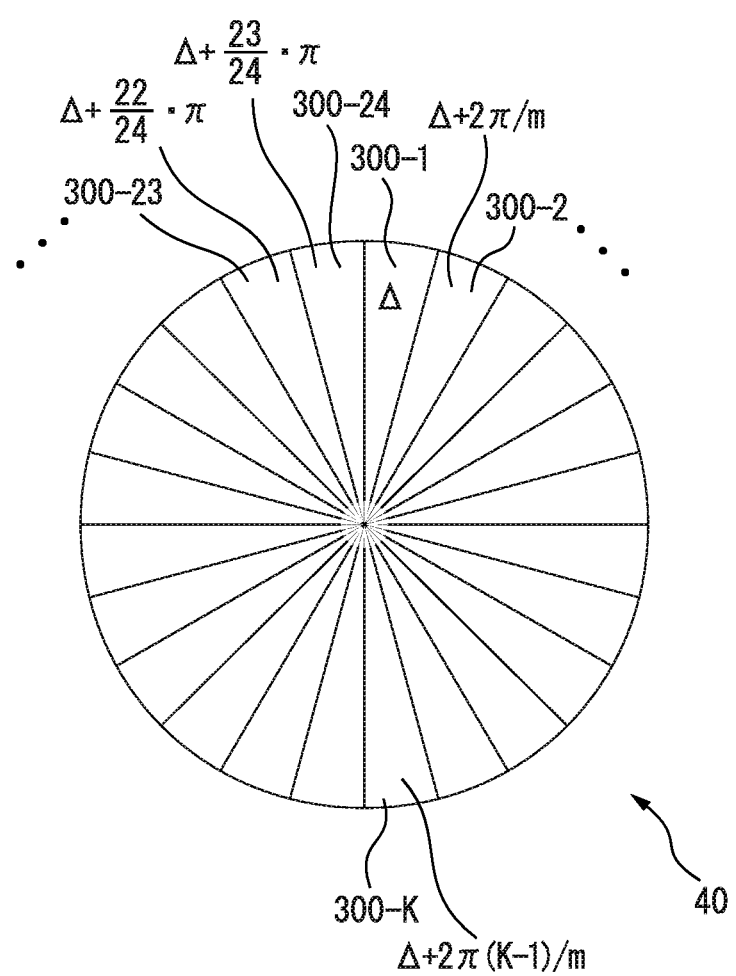
FIG. 3 illustrates an example of amounts of phase modulation provided by the VORTEX liquid crystal element.

FIG. 3 illustrates an example of amounts of phase modulation provided by the VORTEX liquid crystal element 4. FIG. 3 depicts the liquid crystal layer 40 seen from the transparent electrode 43. A partial region 300-$k$ of the liquid crystal layer 40, where k satisfies 1≤k≤m, represents a region between the partial electrode 43-$k$ and the transparent electrode 44.

In the example illustrated in FIG. 3, the amount of phase modulation is increased by 2π over one cycle of turning along the circumference direction around the optical axis OA, i.e., the amount of increase in phase corresponds to the wavelength of linearly polarized light emitted by the light source 1. The amount of increase in phase modulation between adjacent partial regions is expressed by 2π/m. Accordingly, letting Δ be the amount of phase modulation provided by the partial region 300-1, the amount of phase modulation provided by the partial region 300-$k$ is expressed by {Δ+2π(k−1)/m}.

The amount of phase modulation provided by the VORTEX liquid crystal element 4 may be increased around a circle clockwise or counterclockwise. The amount of increase in phase modulation over one cycle of turning along the circumference direction around the optical axis OA is not limited to 2π, and thus the amount of increase may be 4π, 6π, or 8π, for example. It is preferable, however, that the amount of increase in phase modulation over one cycle of turning along the circumference direction around the optical axis OA is an integer multiple of 2π. In addition, any partial region may be the region where a minimum amount of phase modulation is provided by the VORTEX liquid crystal element 4, irrespective of the polarization plane of the incident linearly polarized light.

When a voltage V is applied between the transparent electrodes 43 and 44, the liquid crystal molecules 47 are inclined, in accordance with the voltage V, toward a direction parallel to the direction in which the voltage is applied. The refractive index $n_{\psi(V)}$ of the liquid crystal molecules 47 with respect to a polarized light component in parallel with the direction in which the liquid crystal molecules 47 are aligned is represented as $n_o \leq n_{\psi(V)} \leq n_e$, where $n_o$ is the refractive index with respect to a polarized light component orthogonal to the major axis direction of the liquid crystal molecules, while $n_e$ is the refractive index with respect to a polarized light component in parallel with the major axis direction of the liquid crystal molecules.

Hence, assuming that the liquid crystal molecules 47 included in the liquid crystal layer 40 are homogeneously aligned and that the liquid crystal layer 40 has a thickness d, an optical path length difference $\Delta n d$ ($= n_{\psi(V1)} d - n_{\psi(V2)} d$) is generated between the polarized light component that is parallel to the alignment direction of the liquid crystal molecules 47 and that passes through a partial region where a voltage V1 is applied and the polarized light component that is parallel to the alignment direction of the liquid crystal molecules 47 and that passes through a partial region where a voltage V2 is applied. In other words, a phase difference $2\pi \Delta n d / \lambda$ is generated, where $\lambda$ is the wavelength of a polarized light component. Therefore, the controller 9 can adjust the difference in the amount of phase modulation between partial regions by adjusting the voltage applied between each of the partial electrodes 43-1 to 43-$m$ and the transparent electrode 44.

Preferably, any two adjacent partial electrodes among the multiple partial electrodes 43-1 to 43-$m$ are connected via the same electrical resistance, except for the connection between the partial electrodes 43-1 and 43-$m$, which correspond to the portions representing a minimum amount of phase modulation and a maximum amount of phase modulation, respectively. Thus, the voltage difference between any two adjacent partial regions is uniform except for the voltage difference between the partial regions corresponding to the partial electrodes 43-1 and 43-$m$. Therefore, the controller 9 can apply a voltage corresponding to a minimum amount of phase modulation between the partial electrode 43-1 and the transparent electrode 44, and apply a voltage corresponding to a maximum amount of phase modulation between the partial electrode 43-$m$ and the transparent electrode 44. Thus, the controller 9 can be simpler in configuration.

The individual partial electrodes 43-1 to 43-$m$ may be insulated from one another. In this case, the controller 9 may control the voltage applied to each of the partial electrode 43-1 to 43-$m$ so that each individual partial region can provide a desired amount of phase modulation to the light passing therethrough.

In the present embodiment, the polarization plane of linearly polarized light emitted by the light source 1 is inclined by a predetermined angle $\theta$ relative to the alignment direction of the liquid crystal molecules 47. Hence, the linearly polarized light includes a modulation component, which is a polarized light component having the polarization plane parallel to the alignment direction of the liquid crystal molecules 47, and a non-modulation component, which has the polarization plane orthogonal to the alignment direction and does not undergo phase modulation provided by the VORTEX liquid crystal element 4. When the modulation component passes through the VORTEX liquid crystal element 4, the Gauss beams are transformed into Laguerre-Gauss-like beams. For more information, refer to, for example, Aoki et al. (2014) "Generation and the propagation characteristics of a quantized Laguerre-Gauss beam using liquid crystal optical devices," Proceedings of the 61st the Japan Society of Applied Physics Spring Meeting, 03-024, or Japanese Unexamined Patent Publication (Kokai) No. 2010-247230.

In contrast, the non-modulation component does not undergo any phase modulation provided by the VORTEX liquid crystal element 4. Thus, the non-modulation component keeps its Gauss beams unchanged after passing through the VORTEX liquid crystal element 4.

Figure 4:
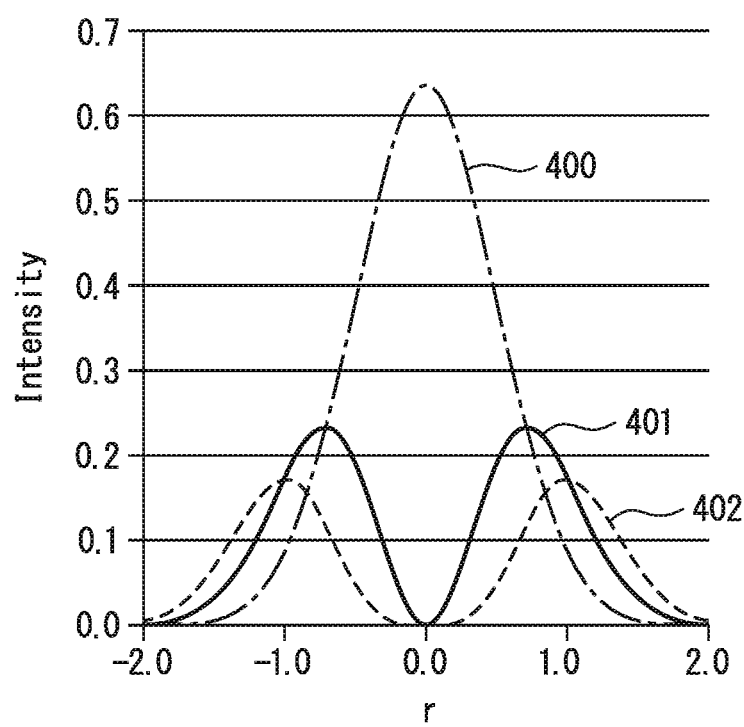
FIG. 4 illustrates an example of a Gauss beam profile and Laguerre-Gauss beam ($LG_{01}$, $LG_{02}$) profiles.

FIG. 4 illustrates an example of a Gauss beam profile and Laguerre-Gauss beam profiles. In FIG. 4, the horizontal axis indicates a distance from the optical axis OA, while the vertical axis indicates a beam intensity. The profile 400 represents a profile of Gauss beams. A Gauss beam corresponds to the $TEM_{00}$ mode, which is a propagation mode, as expressed by the following equation:

$$I(r) = \frac{2}{\pi w^2} \exp\left(-2\frac{r^2}{w^2}\right) \qquad (1)$$

wherein r represents the distance from the optical axis OA, and w is a constant representing the distance from the optical axis OA to a point where the beam intensity falls to 1/e of the maximum value; in other words, w represents the beam diameter. As indicated by the profile 400, the intensity of a Gauss beam decreases with the distance from the optical axis.

The profile 401 represents a profile of Laguerre-Gauss beams $LG_{01}$ corresponding to the $TEM_{01}^*$ mode, which is a propagation mode, as expressed by the following equation:

$$I(r) = \frac{4r^2}{\pi w^4} \exp\left(-2\frac{r^2}{w^2}\right) \qquad (2)$$

The profile 402 represents a profile of Laguerre-Gauss beams $LG_{02}$ corresponding to the $TEM_{02}^*$ mode, which is a propagation mode, as expressed by the following equation:

$$I(r) = \frac{4r^4}{\pi w^6} \exp\left(-2\frac{r^2}{w^2}\right) \qquad (3)$$

As indicated by the profiles 401 and 402, Laguerre-Gauss beams have a cylindrical beam profile where the peak intensity is at a point away from the center by a certain distance. The distance from the optical axis OA to the peak intensity is longer in the Laguerre-Gauss beam $LG_{02}$ than in the Laguerre-Gauss beam $LG_{01}$. Therefore, when combined with a Gauss beam to produce a composite beam, the Laguerre-Gauss beam $LG_{02}$ provides a broader range of flat and relatively high beam intensities than the Laguerre-Gauss beam $LG_{01}$.

When the amount of increase in phase modulation provided by the VORTEX liquid crystal element 4 over one cycle of turning along the circumference direction around the optical axis OA is $2\pi$, which corresponds to the wavelength of linearly polarized light emitted by the light source 1, the modulation component is turned into a Laguerre-Gauss-like beam $LG_{01}'$ whose beam profile approximates to the Laguerre-Gauss beam $LG_{01}$, by passing the linearly polarized light coming from the light source 1 through the VORTEX liquid crystal element 4. When the amount of increase in phase modulation provided by the VORTEX liquid crystal element 4 over one cycle of turning along the circumference direction around the optical axis OA is $4\pi$, which corresponds to twice the wavelength of linearly polarized light emitted by the light source 1, the modulation component is turned into a Laguerre-Gauss-like beam $LG_{02}'$ whose beam profile approximates to the Laguerre-Gauss beam $LG_{02}$, by passing the linearly polarized light coming from the light source 1 through the VORTEX liquid crystal element 4. Therefore, the controller 9 can switch the modulation component to be combined with the non-modulation component, which is a Gauss beam, between the Laguerre-Gauss-like beam $LG_{01}'$ and the Laguerre-Gauss-like beam $LG_{02}'$, by adjusting the voltage applied between the transparent electrode 43 and the transparent electrode 44.

Thus, for example, the memory 10 may store first voltages and second voltages in advance, where the first voltages are applied between the individual partial electrodes of the transparent electrode 43 and the transparent electrode 44 when the modulation component is to be turned into a Laguerre-Gauss-like beam $LG_{01}'$, while the second voltages are applied between the individual partial electrodes of the transparent electrode 43 and the transparent electrode 44 when the modulation component is to be turned into a Laquerre-Gauss-like beam $LG_{02}'$. Then, the controller 9 can adjust the voltage to be applied between each of the partial electrodes of the transparent electrode 43 and the transparent electrode 44 in accordance with the first voltages when the modulation component is to be turned into a Laguerre-Gauss-like beam $LG_{01}'$. Likewise, the controller 9 can adjust the voltage to be applied between each of the partial electrodes of the transparent electrode 43 and the transparent electrode 44 in accordance with the second voltages when the modulation component is to be turned into a Laguerre-Gauss-like beam $LG_{02}'$.

Figure 5:
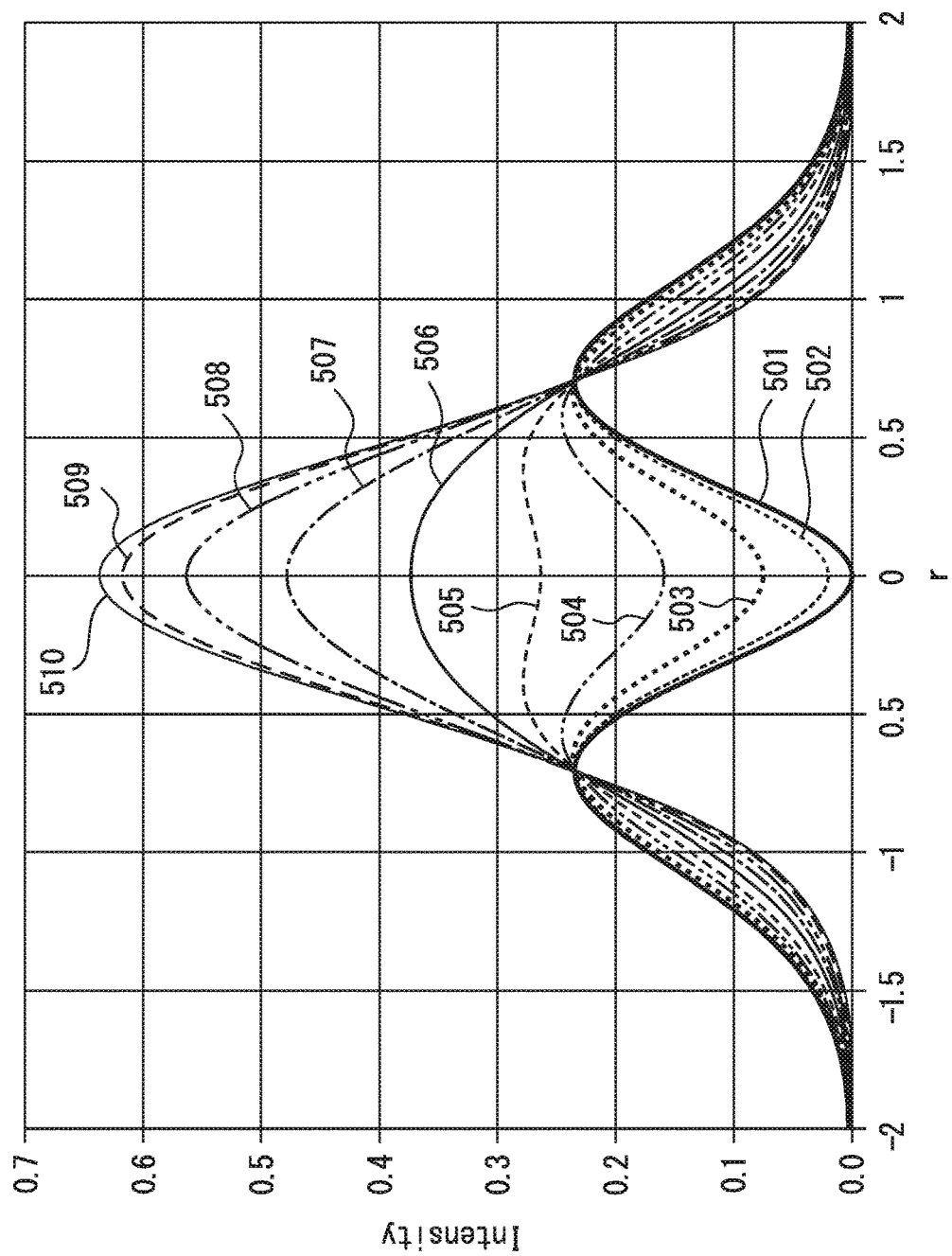
FIG. 5 illustrates a relationship between an angle $\theta$ and a profile of a composite beam, where the angle $\theta$ is formed between the alignment direction of liquid crystal molecules in the VORTEX liquid crystal element and the polarization direction of linearly polarized light coming from the light source, and the composite beam is synthesized from a modulation component and a non-modulation component when the modulation component is turned into a Laguerre-Gauss beam $LG_{01}$.

FIG. 5 illustrates a relationship between an angle θ and a beam profile, where the angle θ is formed between the alignment direction of liquid crystal molecules in the VORTEX liquid crystal element 4 and the polarization direction of linearly polarized light including a first polarized light component and a second polarized light component emitted by the light source, and a beam is obtained by synthesizing from a modulation component and a non-modulation component when the modulation component is turned into, for simplification, a Laguerre-Gauss beam $LG_{01}$. In FIG. 5, the horizontal axis indicates a distance from the optical axis OA, while the vertical axis indicates a beam intensity. Profiles 501 to 510 represent the profiles of composite beams having the respective angles θ ranging from 0° to 90° in increments of 10°. As indicated by the profiles 501 to 510, composite beams having an angle θ falling within a certain range form a top-hat-shaped profile, and a profile of a composite bean is closer to the Laguerre-Gauss beam, as angle θ is smaller.

Figure 6A:
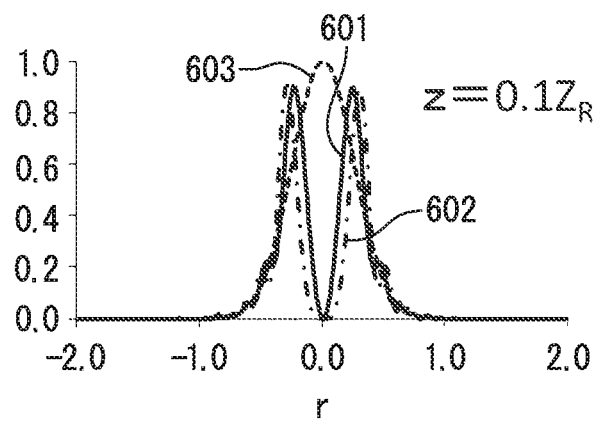
FIG. 6A illustrates a relationship between a propagation distance and a change in the beam profiles of a Gauss beam and a Laguerre-Gauss-like beam.

FIGS. 6A to 6F are diagrams obtained by simulation, each illustrating a relationship between a propagation distance and a change in the beam profiles of a Gauss beam and a Laguerre-Gauss-like beam. In each of FIGS. 6A to 6F, the horizontal axis indicates a distance from the optical axis OA, while the vertical axis indicates a ratio of the intensity of a Laguerre-Gauss-like beam at a point away from the optical axis OA by the distance r to the maximum intensity of a Gauss beam that has passed through the VORTEX liquid crystal element 4. In FIG. 6A ($z=0.1Z_R$), the profile 601 represents the beam profile of a Laguerre-Gauss-like beam $LG_{01}'$, where θ=0° and the propagation distance z from the VORTEX liquid crystal element 4 is 0.1 times the Rayleigh length $Z_R$ ($=k\omega^2/2$), while the profile 602 represents the beam profile of a Laguerre-Gauss-like beam $LG_{02}'$, where θ=0° and the propagation distance z from the VORTEX liquid crystal element 4 is 0.1 times the Rayleigh length $Z_R$. The profile 603 represents the beam profile of a Gauss beam, where θ=90° and the propagation distance z from the VORTEX liquid crystal element 4 is 0.1 times the Rayleigh length $Z_R$.

Figure 6B:
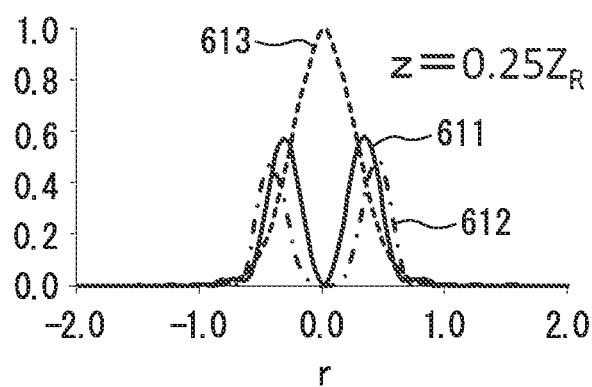
FIG. 6B illustrates a relationship between a propagation distance and a change in the beam profiles of a Gauss beam and a Laguerre-Gauss-like beam.
Figure 6C:
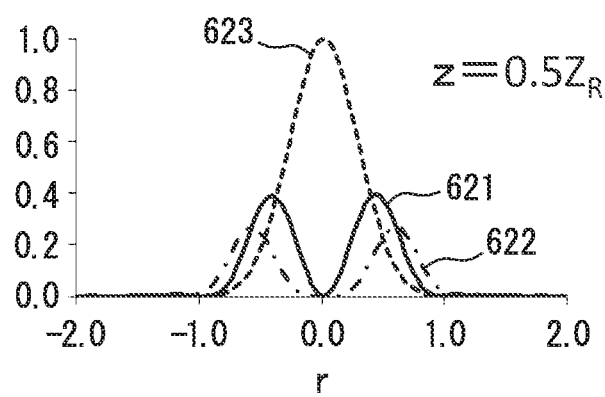
FIG. 6C illustrates a relationship between a propagation distance and a change in the beam profiles of a Gauss beam and a Laguerre-Gauss-like beam.

Likewise, in FIG. 6B ($z=0.25Z_R$), the profile 611 represents the beam profile of a Laguerre-Gauss-like beam $LG_{01}'$, where θ=0° and the propagation distance z from the VORTEX liquid crystal element 4 is 0.25 times the Rayleigh length $Z_R$, while the profile 612 represents the beam profile of a Laguerre-Gauss-like beam $LG_{02}'$, where θ=0° and the propagation distance z from the VORTEX liquid crystal element 4 is 0.25 times the Rayleigh length $Z_R$. The profile 613 represents the beam profile of a Gauss beam, where θ=90° and the propagation distance z from the VORTEX liquid crystal element 4 is 0.25 times the Rayleigh length $Z_R$. In FIG. 6C ($z=0.5Z_R$), the profile 621 represents the beam profile of a Laguerre-Gauss-like beam $LG_{01}'$, where θ=0° and the propagation distance z from the VORTEX liquid crystal element 4 is 0.5 times the Rayleigh length $Z_R$, while the profile 622 represents the beam profile of a Laguerre-Gauss-like beam $LG_{02}'$, where θ=0° and the propagation distance z from the VORTEX liquid crystal element 4 is 0.5 times the Rayleigh length $Z_R$. The profile 623 represents the beam profile of a Gauss beam, where θ=90° and the propagation distance z from the VORTEX liquid crystal element 4 is 0.5 times the Rayleigh length $Z_R$.

Figure 6D:
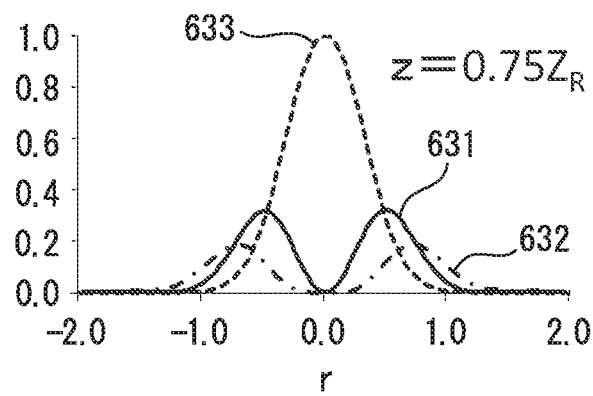
FIG. 6D illustrates a relationship between a propagation distance and a change in the beam profiles of a Gauss beam and a Laguerre-Gauss-like beam.
Figure 6E:
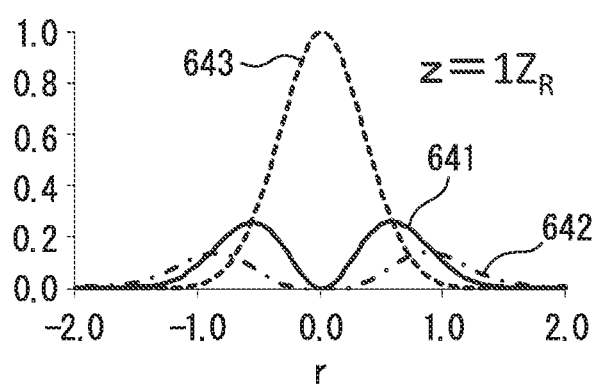
FIG. 6E illustrates a relationship between a propagation distance and a change in the beam profiles of a Gauss beam and a Laguerre-Gauss-like beam.
Figure 6F:
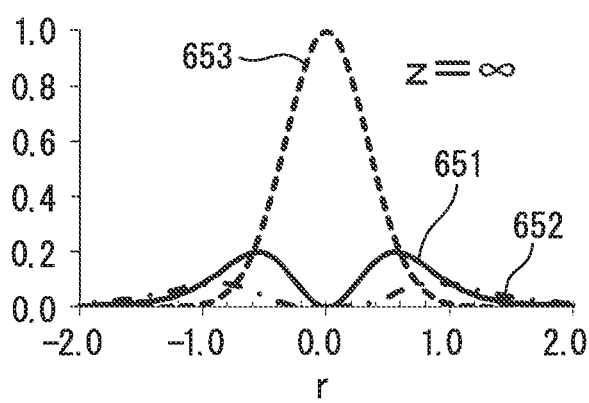
FIG. 6F illustrates a relationship between a propagation distance and a change in the beam profiles of a Gauss beam and a Laguerre-Gauss-like beam.

In FIG. 6D ($z=0.75Z_R$), the profile 631 represents the beam profile of a Laguerre-Gauss-like beam $LG_{01}'$, where θ=0° and the propagation distance z from the VORTEX liquid crystal element 4 is 0.75 times the Rayleigh length $Z_R$, while the profile 632 represents the beam profile of a Laguerre-Gauss-like beam $LG_{02}'$, where θ=0° and the propagation distance z from the VORTEX liquid crystal element 4 is 0.75 times the Rayleigh length $Z_R$. The profile 633 represents the beam profile of a Gauss beam, where θ=90° and the propagation distance z from the VORTEX liquid crystal element 4 is 0.75 times the Rayleigh length $Z_R$. In FIG. 6E ($z=Z_R$), the profile 641 represents the beam profile of a Laguerre-Gauss-like beam $LG_{01}'$, where θ=0° and the propagation distance z from the VORTEX liquid crystal element 4 is equal to the Rayleigh length $Z_R$, while the profile 642 represents the beam profile of a Laguerre-Gauss-like beam $LG_{02}'$, where θ=0° and the propagation distance z from the VORTEX liquid crystal element 4 is equal to the Rayleigh length $Z_R$. The profile 643 represents the beam profile of a Gauss beam, where θ=90° and the propagation distance z from the VORTEX liquid crystal element 4 is equal to the Rayleigh length $Z_R$. In FIG. 6F ($z=\infty$), the profile 651 represents the beam profile of a Laguerre-Gauss-like beam $LG_{01}'$, where θ=0° and the propagation distance z from the VORTEX liquid crystal element 4 is infinite, while the profile 652 represents the beam profile of a Laguerre-Gauss-like beam $LG_{02}'$, where θ=0° and the propagation distance z from the VORTEX liquid crystal element 4 is infinite. The profile 653 represents the beam profile of a Gauss beam, where θ=90° and the propagation distance z from the VORTEX liquid crystal element 4 is infinite.

As indicated in FIGS. 6A to 6F, both the Laguerre-Gauss-like beams $LG_{01}'$ and $LG_{02}'$ have a larger side lobe and a lower peak intensity as the propagation distance is longer. This is because both of the Laguerre-Gauss-like beams $LG_{01}'$ and $LG_{02}'$ produced by passing a Gauss beam through the VORTEX liquid crystal element 4 are not the exact Laguerre-Gauss beam, which means the Laguerre-Gauss-like beams $LG_{01}'$ and $LG_{02}'$ contain a higher-order component other than $LG_{01}$ and $LG_{02}$, and under the influence of such higher-order component, $LG_{01}'$ and $LG_{02}'$ are more deviated from $LG_{01}$ and $LG_{02}$ depending on the propagation distance.

This indicates that an optimum angle θ for forming a top-hat beam continuously changes depending on the propagation distance of Laguerre-Gauss-like beams $LG_{01}'$ and $LG_{02}'$. In other words, the illumination device 11 can form a top-hat beam at a desired propagation distance by making the angle θ smaller as a propagation distance is longer, so that Laguerre-Gauss-like beams $LG_{01}'$ and $LG_{02}'$ have a higher intensity relative to the Gauss beam.

The Strehl ratio in relation to an acceptable range of the angle θ is discussed. The Strehl ratio, which is an index expressing performance of an optical imaging system, is a ratio of a peak brightness on an image made by light coming from a point light source in an optical system to a peak brightness in a diffraction-limited system. Thus, an optical system having a Strehl ratio closer to 1 offers higher imaging performance. In general, an influence of residual aberrations on imaging performance may be ignored when the Strehl ratio is 0.8 or above (see, for example, Kishikawa, T., *Yuuza Enjinia no tame no Kogaku Nyumon* (Introduction to Optics for User Engineers), Optronics, p. 198). Therefore, for a spinning confocal microscope, for example, the illumination light incident on each pinhole in the mask plate preferably has an intensity of at least 0.8 times the maximum intensity of the illumination light.

Accordingly, the composite beam is needed to have an intensity of at least 0.8 times its maximum intensity within, for example, the full width at half maximum (hereinafter denoted as FWHM) of a Gauss beam that has passed through the VORTEX liquid crystal element 4. Note here that a wavefront error will arise from a Gauss beam emitted by the light source 1 passing through the VORTEX liquid crystal element 4, because the VORTEX liquid crystal element 4 changes the amount of phase modulation not continuously but discretely. Because of the wavefront error, an intensity error is to occur between an intensity of a Laguerre-Gauss-like beam to which continuous phases are given (hereinafter referred to as a theoretical intensity) and an intensity of a Laguerre-Gauss-like beam to which discrete phases are given (hereinafter referred to as an actual intensity). An error ratio of the intensity error can be expressed by "(actual intensity)/theoretical intensity)". In view of the error ratio of the intensity error, a value calculated by dividing the intensity of a composite beam by the error ratio is needed to be at least 0.8 times the maximum intensity of the composite beam. For example, when the transparent electrode 43 includes 24 partial electrodes, in other words, when the amount of phase modulation changes in 24 steps over the whole circumference, the wavefront error reduces the maximum intensity of a Laguerre-Gauss-like beam $LG_{01}'$ to about 0.98 times the maximum intensity involving no wavefront error. Accordingly, the actual intensity of a resulting composite beam within the FWHM is regarded as at least 0.8 times the maximum intensity when the theoretical intensity of the composite beam is at least 0.78 times the maximum intensity.

Figure 7A:
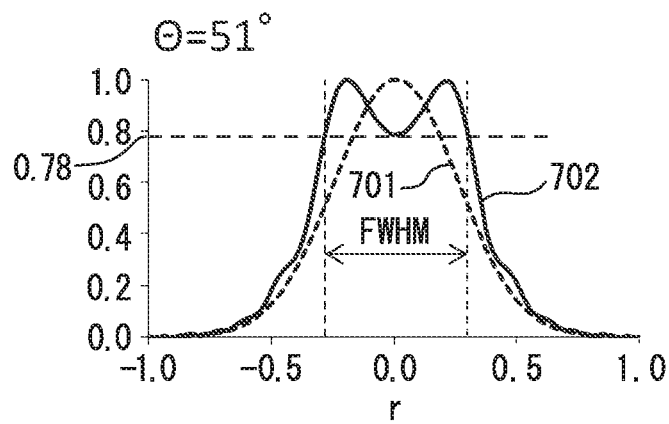
FIG. 7A illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the propagation distance from the VORTEX liquid crystal element to the observation plane is 0.1 times the Rayleigh length, and the angle $\theta$ formed between the alignment direction of liquid crystal molecules in the VORTEX liquid crystal element and the polarization direction of the Gauss beam emitted by the light source is 51°.
Figure 7B:
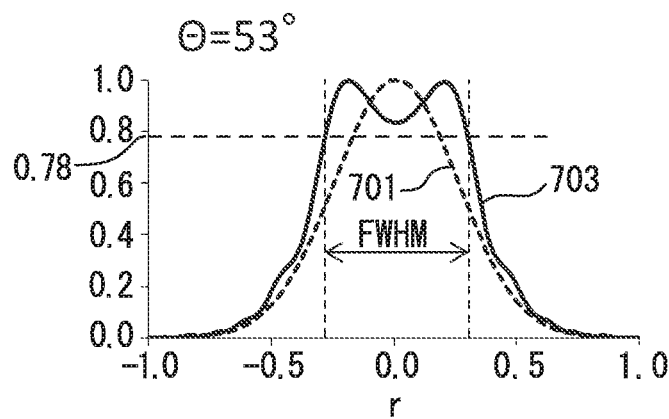
FIG. 7B illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the propagation distance from the VORTEX liquid crystal element to the observation plane is 0.1 times the Rayleigh length, and the angle $\theta$ formed between the alignment direction of liquid crystal molecules in the VORTEX liquid crystal element and the polarization direction of the Gauss beam emitted by the light source is 53°.
Figure 7C:
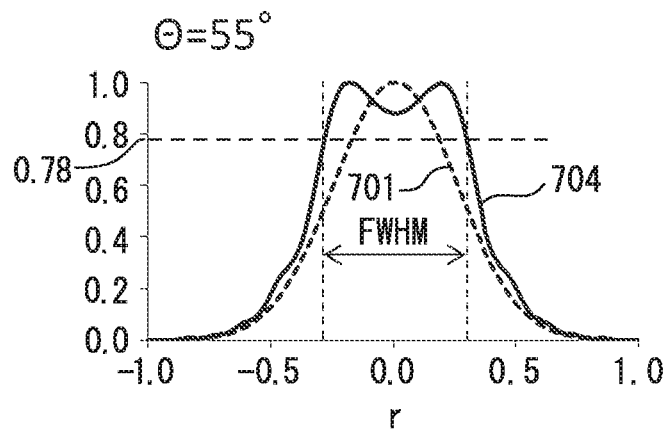
FIG. 7C illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the propagation distance from the VORTEX liquid crystal element to the observation plane is 0.1 times the Rayleigh length, and the angle θ formed between the alignment direction of liquid crystal molecules in the VORTEX liquid crystal element and the polarization direction of the Gauss beam emitted by the light source is 55°.

FIGS. 7A to 7C are diagrams obtained by simulation, each illustrating a relationship between the profile of a composite beam synthesized from a Gauss beam that has passed through the VORTEX liquid crystal element 4 and from a Laguerre-Gauss-like beam $LG_{01}'$ and the FWHM of the Gauss beam that has passed through the VORTEX liquid crystal element 4, where the propagation distance from the VORTEX liquid crystal element to the observation plane (i.e., the plane irradiated with the composite beam) is 0.1 times the Rayleigh length $Z_R$, and the angle θ formed between the alignment direction of liquid crystal molecules in the VORTEX liquid crystal element 4 and the polarization direction of the Gauss beam emitted by the light source 1 is 51°, 53°, or 55°. In each of FIGS. 7A to 7C, the horizontal axis indicates a distance from the optical axis OA, while the vertical axis indicates a ratio of the intensity of the composite beam at a point away from the optical axis OA by the distance r to its maximum intensity. The profile 701 represents the profile of a Gauss beam that has passed through the VORTEX liquid crystal element 4, while the profiles 702 to 704 represent the profiles of composite beams corresponding to angles θ of 51°, 530, and 550, respectively. As indicated in FIGS. 7A to 7C, the ratio of the theoretical intensity of a composite beam to its maximum theoretical intensity is at least 0.78 within the FWHM when the angle θ is at least 51° and not greater than 55°. In other words, the actual intensity of the composite beam is presumably at least 0.8 times its maximum intensity within the FWHM. Therefore, in this case, it is preferable that the angle θ satisfies $51° \leq θ \leq 55°$.

Figure 8A:
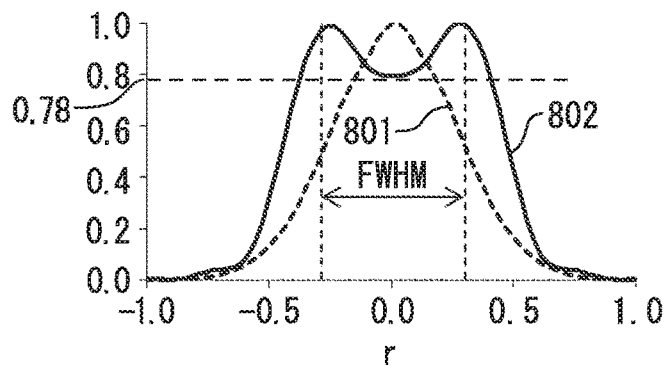
FIG. 8A illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the propagation distance from the VORTEX liquid crystal element to the observation plane is 0.25 times the Rayleigh length, and the angle θ formed between the alignment direction of liquid crystal molecules in the VORTEX liquid crystal element and the polarization direction of the Gauss beam emitted by the light source is 41°.
Figure 8B:
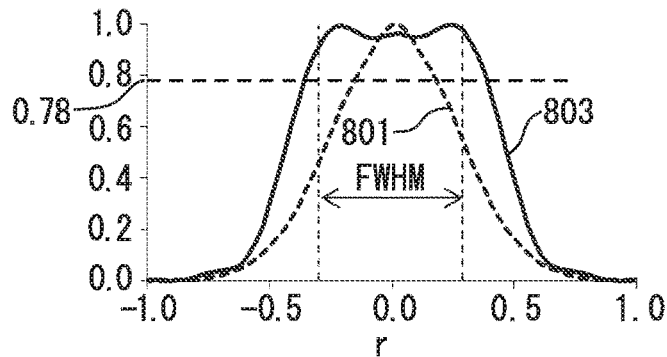
FIG. 8B illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the propagation distance from the VORTEX liquid crystal element to the observation plane is 0.25 times the Rayleigh length, and the angle θ formed between the alignment direction of liquid crystal molecules in the VORTEX liquid crystal element and the polarization direction of the Gauss beam emitted by the light source is 47°.
Figure 8C:
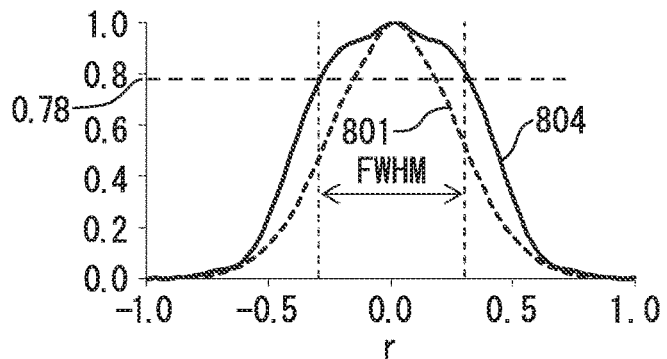
FIG. 8C illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the propagation distance from the VORTEX liquid crystal element to the observation plane is 0.25 times the Rayleigh length, and the angle θ formed between the alignment direction of liquid crystal molecules in the VORTEX liquid crystal element and the polarization direction of the Gauss beam emitted by the light source is 54°.

FIGS. 8A to 8C are diagrams obtained by simulation, each illustrating a relationship between the profile of a composite beam synthesized from a Gauss beam that has passed through the VORTEX liquid crystal element 4 and from a Laguerre-Gauss-like beam $LG_{01}'$ and the FWHM of the Gauss beam that has passed through the VORTEX liquid crystal element 4, where the propagation distance from the VORTEX liquid crystal element 4 to the observation plane is 0.25 times the Rayleigh length $Z_R$, and the angle θ formed between the alignment direction of liquid crystal molecules in the VORTEX liquid crystal element 4 and the polarization direction of the Gauss beam emitted by the light source 1 is 41°, 47°, or 54°. In each of FIGS. 8A to 8C, the horizontal axis indicates a distance from the optical axis OA, while the vertical axis indicates a ratio of the intensity of the composite beam at a point away from the optical axis OA by the distance r to its maximum intensity. The profile 801 represents the profile of a Gauss beam that has passed through the VORTEX liquid crystal element 4, while the profiles 802 to 804 represent the profiles of composite beams corresponding to angles θ of 41°, 47°, and 54°, respectively. As indicated in FIGS. 8A to 8C, the ratio of the theoretical intensity of a composite beam to its maximum theoretical intensity is at least 0.78 within the FWHM when the angle θ is at least 41° and not greater than 54°. Therefore, in this case, it is preferable that the angle θ satisfies $41° \leq θ \leq 54°$.

Figure 9A:
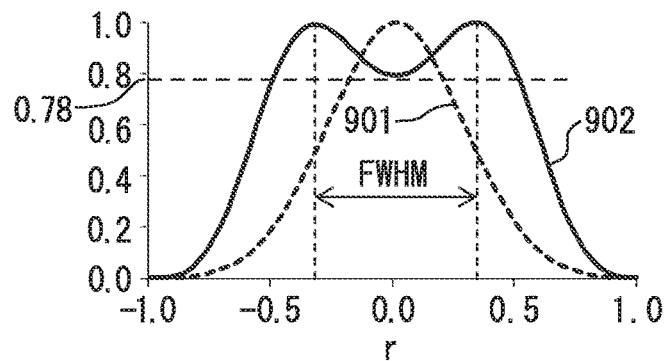
FIG. 9A illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the propagation distance from the VORTEX liquid crystal element to the observation plane is 0.5 times the Rayleigh length, and the angle θ formed between the alignment direction of liquid crystal molecules in the VORTEX liquid crystal element and the polarization direction of the Gauss beam emitted by the light source is 34°.
Figure 9B:
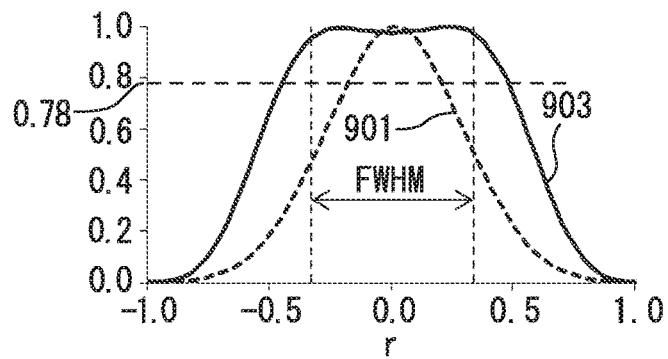
FIG. 9B illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the propagation distance from the VORTEX liquid crystal element to the observation plane is 0.5 times the Rayleigh length, and the angle θ formed between the alignment direction of liquid crystal molecules in the VORTEX liquid crystal element and the polarization direction of the Gauss beam emitted by the light source is 41°.
Figure 9C:
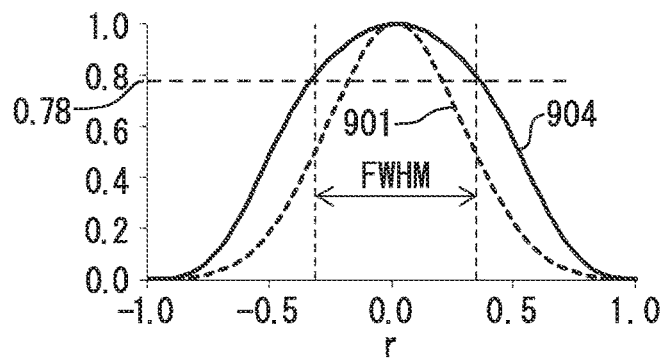
FIG. 9C illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the propagation distance from the VORTEX liquid crystal element to the observation plane is 0.5 times the Rayleigh length, and the angle θ formed between the alignment direction of liquid crystal molecules in the VORTEX liquid crystal element and the polarization direction of the Gauss beam emitted by the light source is 47°.

FIGS. 9A to 9C are diagrams obtained by simulation, each illustrating a relationship between the profile of a composite beam synthesized from a Gauss beam that has passed through the VORTEX liquid crystal element 4 and from a Laguerre-Gauss-like beam $LG_{01}'$ and the FWHM of the Gauss beam that has passed through the VORTEX liquid crystal element 4, where the propagation distance from the VORTEX liquid crystal element 4 to the observation plane is 0.5 times the Rayleigh length, and the angle θ formed between the alignment direction of liquid crystal molecules in the VORTEX liquid crystal element 4 and the polarization direction of the Gauss beam emitted by the light source 1 is 34°, 41°, or 47°. In each of FIGS. 9A to 9C, the horizontal axis indicates a distance from the optical axis OA, while the vertical axis indicates a ratio of the intensity of the composite beam at a point away from the optical axis OA by the distance r to its maximum intensity. The profile 901 represents the profile of a Gauss beam that has passed through the VORTEX liquid crystal element 4, while the profiles 902 to 904 represent the profiles of composite beams corresponding to angles θ of 34°, 41°, and 47°, respectively. As indicated in FIGS. 9A to 9C, the ratio of the theoretical intensity of a composite beam to its maximum theoretical intensity is at least 0.78 within the FWHM when the angle θ is at least 34° and not greater than 47°. Therefore, in this case, it is preferable that the angle θ satisfies 34°≤θ≤47°.

Figure 10A:
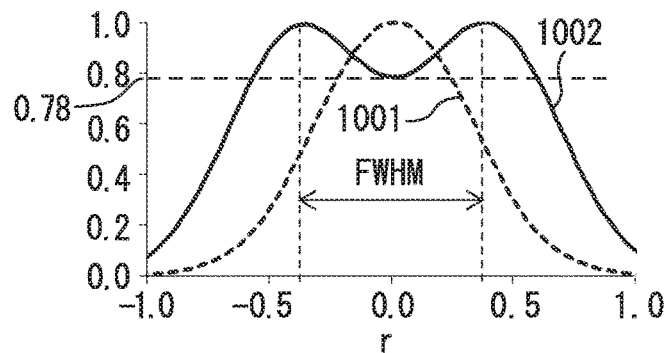
FIG. 10A illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the propagation distance from the VORTEX liquid crystal element to the observation plane is 0.75 times the Rayleigh length, and the angle θ formed between the alignment direction of liquid crystal molecules in the VORTEX liquid crystal element and the polarization direction of the Gauss beam emitted by the light source is 31°.
Figure 10B:
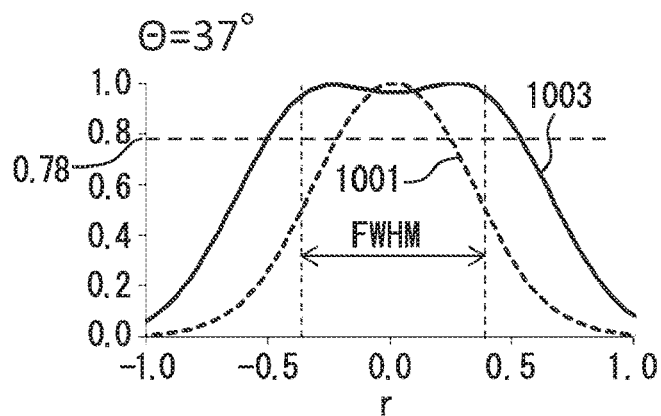
FIG. 10B illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the propagation distance from the VORTEX liquid crystal element to the observation plane is 0.75 times the Rayleigh length, and the angle θ formed between the alignment direction of liquid crystal molecules in the VORTEX liquid crystal element and the polarization direction of the Gauss beam emitted by the light source is 37°.
Figure 10C:
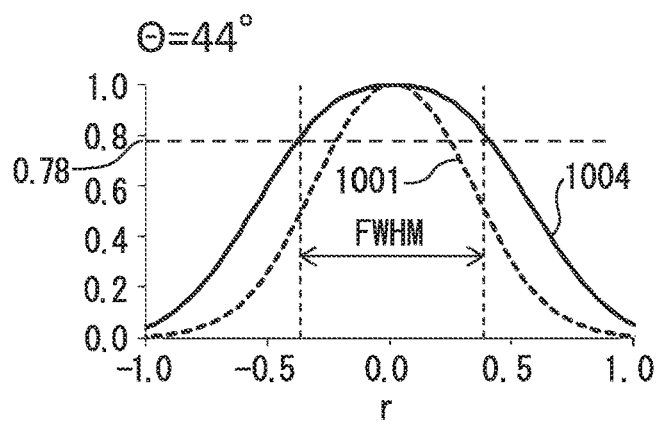
FIG. 10C illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the propagation distance from the VORTEX liquid crystal element to the observation plane is 0.75 times the Rayleigh length, and the angle θ formed between the alignment direction of liquid crystal molecules in the VORTEX liquid crystal element and the polarization direction of the Gauss beam emitted by the light source is 44°.

FIGS. 10A to 10C are diagrams obtained by simulation, each illustrating a relationship between the profile of a composite beam synthesized from a Gauss beam that has passed through the VORTEX liquid crystal element 4 and from a Laguerre-Gauss-like beam $LG_{01}'$ and the FWHM of the Gauss beam that has passed through the VORTEX liquid crystal element 4, where the propagation distance from the VORTEX liquid crystal element 4 to the observation plane is 0.75 times the Rayleigh length, and the angle θ formed between the alignment direction of liquid crystal molecules in the VORTEX liquid crystal element 4 and the polarization direction of the Gauss beam emitted by the light source 1 is 31°, 37°, or 44°. In each of FIGS. 10A to 10C, the horizontal axis indicates a distance from the optical axis OA, while the vertical axis indicates a ratio of the intensity of the composite beam at a point away from the optical axis OA by the distance r to its maximum intensity. The profile 1001 represents the profile of a Gauss beam that has passed through the VORTEX liquid crystal element 4, while the profiles 1002 to 1004 represent the profiles of composite beams corresponding to angles θ of 31°, 37°, and 44°, respectively. As indicated in FIGS. 10A to 10C, the ratio of the theoretical intensity of a composite beam to its maximum theoretical intensity is at least 0.78 within the FWHM when the angle θ is at least 31° and not greater than 44°. Therefore, in this case, it is preferable that the angle θ satisfies 31°≤θ≤44°.

FIGS. 11A to 11C are diagrams obtained by simulation, each illustrating a relationship between the profile of a composite beam synthesized from a Gauss beam that has passed through the VORTEX liquid crystal element 4 and from a Laguerre-Gauss-like beam $LG_{01}'$ and the FWHM of the Gauss beam that has passed through the VORTEX liquid crystal element 4, where the propagation distance from the VORTEX liquid crystal element 4 to the observation plane is equal to the Rayleigh length, and the angle θ formed between the alignment direction of liquid crystal molecules in the VORTEX liquid crystal element 4 and the polarization direction of the Gauss beam emitted by the light source 1 is 28°, 34°, or 41°. In each of FIGS. 11A to 11C, the horizontal axis indicates a distance from the optical axis OA, while the vertical axis indicates a ratio of the intensity of the composite beam at a point away from the optical axis OA by the distance r to its maximum intensity. The profile 1101 represents the profile of a Gauss beam that has passed through the VORTEX liquid crystal element 4, while the profiles 1102 to 1104 represent the profiles of composite beams corresponding to angles θ of 28°, 34°, and 41°, respectively. As indicated in FIGS. 11A to 11C, the ratio of the theoretical intensity of a composite beam to its maximum theoretical intensity is at least 0.78 within the FWHM when the angle θ is at least 28° and not greater than 41°. Therefore, in this case, it is preferable that the angle θ satisfies 28°≤θ≤41°.

Figure 12A:
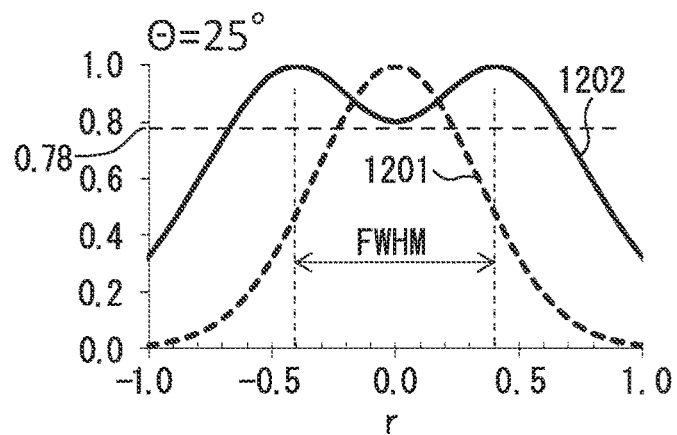
FIG. 12A illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the observation plane is positioned far from the VORTEX liquid crystal element, and the angle θ formed between the alignment direction of liquid crystal molecules in the VORTEX liquid crystal element and the polarization direction of the Gauss beam emitted by the light source is 25°.
Figure 12B:
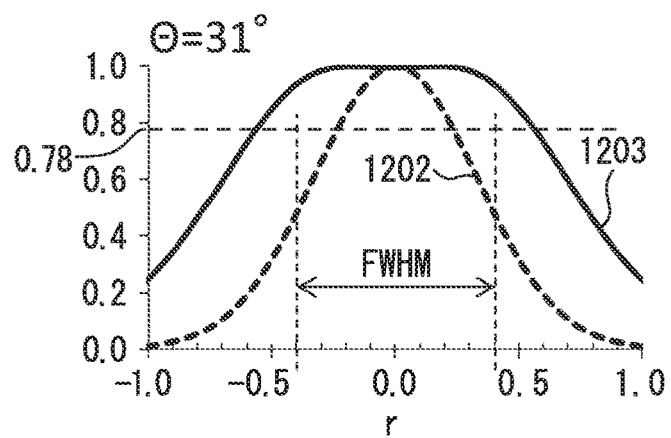
FIG. 12B illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the observation plane is positioned far from the VORTEX liquid crystal element, and the angle θ formed between the alignment direction of liquid crystal molecules in the VORTEX liquid crystal element and the polarization direction of the Gauss beam emitted by the light source is 31°.
Figure 12C:
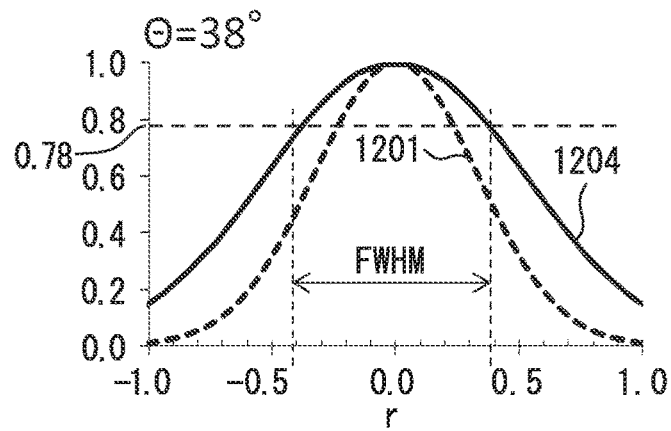
FIG. 12C illustrates a relationship between the profile of a composite beam synthesized from a Gauss beam that has passed through the VORTEX liquid crystal element and from a Laguerre-Gauss-like beam $LG_{01}'$ and the FWHM of the Gauss beam that has passed through the VORTEX liquid crystal element, where the observation plane is positioned far from the VORTEX liquid crystal element, and the angle θ formed between the alignment direction of liquid crystal molecules in the VORTEX liquid crystal element and the polarization direction of the Gauss beam emitted by the light source is 38°.

FIGS. 12A to 12C are diagrams obtained by simulation, each illustrating a relationship between the profile of a composite beam synthesized from a Gauss beam that has passed through the VORTEX liquid crystal element 4 and from a Laguerre-Gauss-like beam $LG_{01}'$ and the FWHM of the Gauss beam that has passed through the VORTEX liquid crystal element 4, where the observation plane is far enough (i.e., far enough to be regarded as infinity) from the VORTEX liquid crystal element 4, and the angle θ formed between the alignment direction of liquid crystal molecules in the VORTEX liquid crystal element 4 and the polarization direction of the Gauss beam emitted by the light source 1 is 25°, 31°, or 38°. In each of FIGS. 12A to 12C, the horizontal axis indicates a distance from the optical axis OA, while the vertical axis indicates a ratio of the intensity of the composite beam at a point away from the optical axis OA by the distance r to its maximum intensity. The profile 1201 represents the profile of a Gauss beam that has passed through the VORTEX liquid crystal element 4, while the profiles 1202 to 1204 represent the profiles of composite beams corresponding to angles θ of 25°, 31°, and 38°, respectively. As indicated in FIGS. 12A to 12C, the ratio of the theoretical intensity of a composite beam to its maximum theoretical intensity is at least 0.78 within the FWHM when the angle θ is at least 25° and not greater than 38°. Therefore, in this case, it is preferable that the angle θ satisfies 25°≤θ≤38°.

As with the Laguerre-Gauss-like beam $LG_{02}'$, a wavefront error reduces the maximum intensity of a Laguerre-Gauss-like beam $LG_{02}'$ to about 0.90 times the maximum intensity involving no wavefront error. Accordingly, the actual intensity of a resulting composite beam within the FWHM is regarded as at least 0.8 times the maximum intensity when the theoretical intensity of the composite beam is at least 0.72 times the maximum intensity.

Figure 13A:
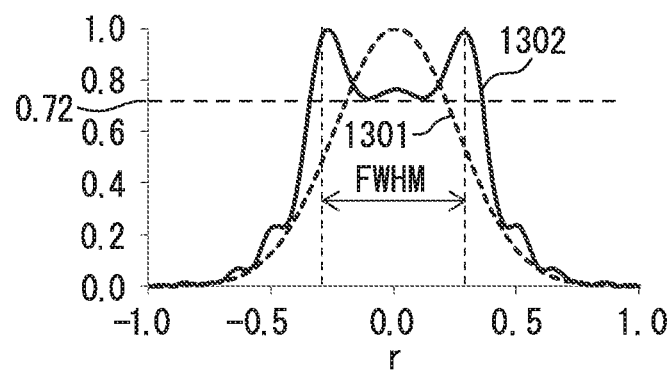
FIG. 13A is a diagram obtained by simulation, illustrating a relationship between the profile of a composite beam synthesized from a Gauss beam that has passed through the VORTEX liquid crystal element and from a Laguerre-Gauss-like beam $LG_{02}'$ and the FWHM of the Gauss beam that has passed through the VORTEX liquid crystal element, where the propagation distance from the VORTEX liquid crystal element to the observation plane is 0.1 times the Rayleigh length, and the angle θ formed between the alignment direction of liquid crystal molecules in the VORTEX liquid crystal element and the polarization direction of the Gauss beam emitted by the light source is 47°.
Figure 13B:
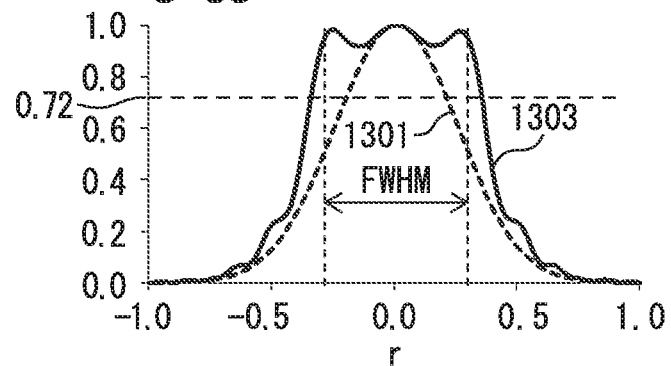
FIG. 13B is a diagram obtained by simulation, illustrating a relationship between the profile of a composite beam synthesized from a Gauss beam that has passed through the VORTEX liquid crystal element and from a Laguerre-Gauss-like beam $LG_{02}'$ and the FWHM of the Gauss beam that has passed through the VORTEX liquid crystal element, where the propagation distance from the VORTEX liquid crystal element to the observation plane is 0.1 times the Rayleigh length, and the angle θ formed between the alignment direction of liquid crystal molecules in the VORTEX liquid crystal element and the polarization direction of the Gauss beam emitted by the light source is 55°.
Figure 13C:
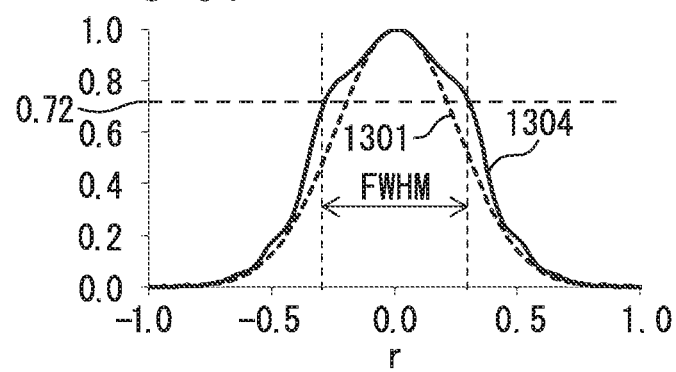
FIG. 13C is a diagram obtained by simulation, illustrating a relationship between the profile of a composite beam synthesized from a Gauss beam that has passed through the VORTEX liquid crystal element and from a Laguerre-Gauss-like beam $LG_{02}'$ and the FWHM of the Gauss beam that has passed through the VORTEX liquid crystal element, where the propagation distance from the VORTEX liquid crystal element to the observation plane is 0.1 times the Rayleigh length, and the angle θ formed between the alignment direction of liquid crystal molecules in the VORTEX liquid crystal element and the polarization direction of the Gauss beam emitted by the light source is 64°.

FIGS. 13A to 13C are diagrams obtained by simulation, each illustrating a relationship between the profile of a composite beam synthesized from a Gauss beam that has passed through the VORTEX liquid crystal element 4 and from a Laguerre-Gauss-like beam $LG_{02}'$ and the FWHM of the Gauss beam that has passed through the VORTEX liquid crystal element 4, where the propagation distance from the VORTEX liquid crystal element 4 to the observation plane is 0.1 times the Rayleigh length $Z_R$, and the angle θ formed between the alignment direction of liquid crystal molecules in the VORTEX liquid crystal element 4 and the polarization direction of the Gauss beam emitted by the light source 1 is 47°, 55°, or 64°. In each of FIGS. 13A to 13C, the horizontal axis indicates a distance from the optical axis OA, while the vertical axis indicates a ratio of the intensity of the composite beam at a point away from the optical axis OA by the distance r to its maximum intensity. The profile 1301 represents the profile of a Gauss beam that has passed through the VORTEX liquid crystal element 4, while the profiles 1302 to 1304 represent the profiles of composite beams corresponding to angles θ of 47°, 55°, and 64°, respectively. As indicated in FIGS. 13A to 13C, the ratio of the theoretical intensity of a composite beam to its maximum theoretical intensity is at least 0.72 within the FWHM when the angle θ is at least 47° and not greater than 64°. In other words, the actual intensity of the composite beam is presumably at least 0.8 times its maximum intensity within the FWHM. Therefore, in this case, it is preferable that the angle θ satisfies 47°≤θ≤64°.

Figure 14A:
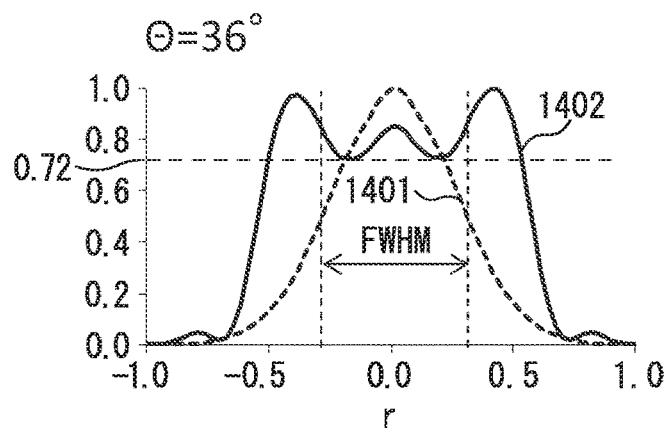
FIG. 14A is a diagram obtained by simulation, illustrating a relationship between the profile of a composite beam synthesized from a Gauss beam that has passed through the VORTEX liquid crystal element and from a Laguerre-Gauss-like beam $LG_{02}'$ and the FWHM of the Gauss beam that has passed through the VORTEX liquid crystal element, where the propagation distance from the VORTEX liquid crystal element to the observation plane is 0.25 times the Rayleigh length, and the angle θ formed between the alignment direction of liquid crystal molecules in the VORTEX liquid crystal element and the polarization direction of the Gauss beam emitted by the light source is 36°.
Figure 14B:
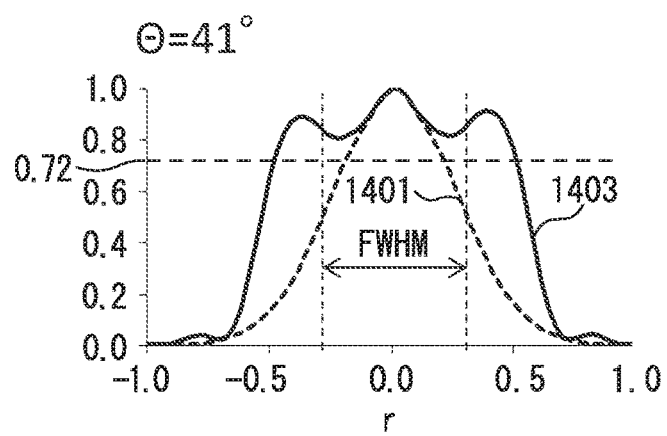
FIG. 14B is a diagram obtained by simulation, illustrating a relationship between the profile of a composite beam synthesized from a Gauss beam that has passed through the VORTEX liquid crystal element and from a Laguerre-Gauss-like beam $LG_{02}'$ and the FWHM of the Gauss beam that has passed through the VORTEX liquid crystal element, where the propagation distance from the VORTEX liquid crystal element to the observation plane is 0.25 times the Rayleigh length, and the angle θ formed between the alignment direction of liquid crystal molecules in the VORTEX liquid crystal element and the polarization direction of the Gauss beam emitted by the light source is 41°.
Figure 14C:
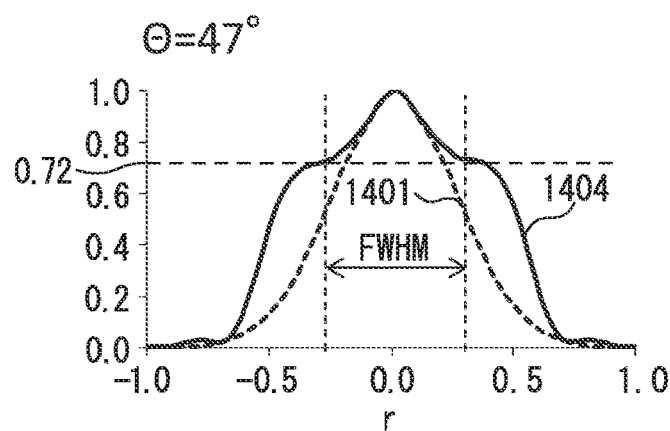
FIG. 14C is a diagram obtained by simulation, illustrating a relationship between the profile of a composite beam synthesized from a Gauss beam that has passed through the VORTEX liquid crystal element and from a Laguerre-Gauss-like beam $LG_{02}'$ and the FWHM of the Gauss beam that has passed through the VORTEX liquid crystal element, where the propagation distance from the VORTEX liquid crystal element to the observation plane is 0.25 times the Rayleigh length, and the angle θ formed between the alignment direction of liquid crystal molecules in the VORTEX liquid crystal element and the polarization direction of the Gauss beam emitted by the light source is 47°.

FIGS. 14A to 14C are diagrams obtained by simulation, each illustrating a relationship between the profile of a composite beam synthesized from a Gauss beam that has passed through the VORTEX liquid crystal element 4 and from a Laguerre-Gauss-like beam $LG_{02}'$ and the FWHM of the Gauss beam that has passed through the VORTEX liquid crystal element 4, where the propagation distance from the VORTEX liquid crystal element 4 to the observation plane is 0.25 times the Rayleigh length $Z_R$, and the angle θ formed between the alignment direction of liquid crystal molecules in the VORTEX liquid crystal element 4 and the polarization direction of the Gauss beam emitted by the light source 1 is 36°, 41°, or 47°. In each of FIGS. 14A to 14C, the horizontal axis indicates a distance from the optical axis OA, while the vertical axis indicates a ratio of the intensity of the composite beam at a point away from the optical axis OA by the distance r to its maximum intensity. The profile 1401 represents the profile of a Gauss beam that has passed through the VORTEX liquid crystal element 4, while the profiles 1402 to 1404 represent the profiles of composite beams corresponding to angles θ of 36°, 41°, and 47°, respectively. As indicated in FIGS. 14A to 14C, the ratio of the theoretical intensity of a composite beam to its maximum theoretical intensity is at least 0.72 within the FWHM when the angle θ is at least 36° and not greater than 47°. Therefore, in this case, it is preferable that the angle θ satisfies 36°≤θ≤47°.

Figure 15A:
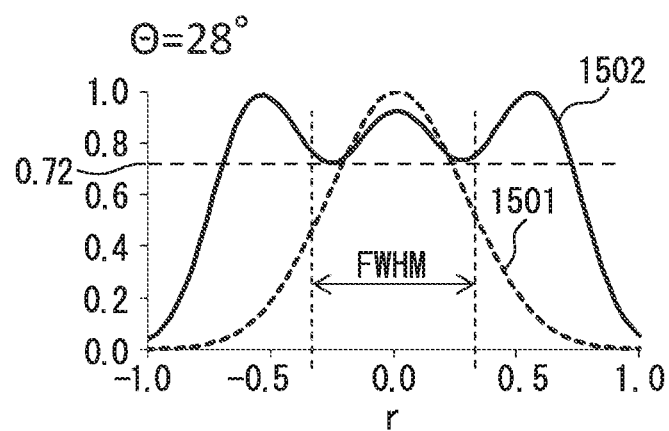
FIG. 15A is a diagram obtained by simulation, illustrating a relationship between the profile of a composite beam synthesized from a Gauss beam that has passed through the VORTEX liquid crystal element and from a Laguerre-Gauss-like beam $LG_{02}'$ and the FWHM of the Gauss beam that has passed through the VORTEX liquid crystal element, where the propagation distance from the VORTEX liquid crystal element to the observation plane is 0.5 times the Rayleigh length, and the angle θ formed between the alignment direction of liquid crystal molecules in the VORTEX liquid crystal element and the polarization direction of the Gauss beam emitted by the light source is 28°.
Figure 15B:
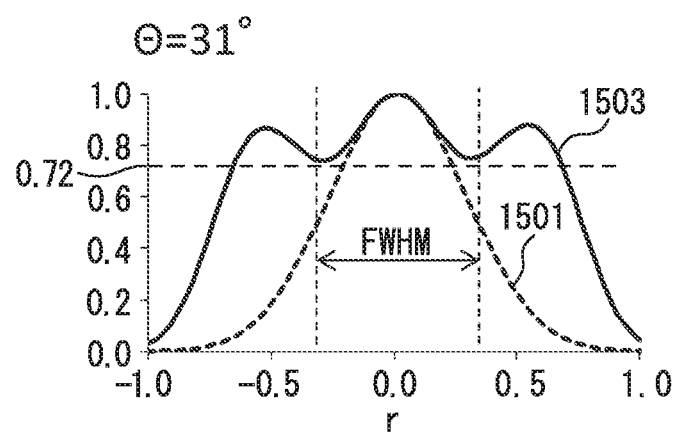
FIG. 15B is a diagram obtained by simulation, illustrating a relationship between the profile of a composite beam synthesized from a Gauss beam that has passed through the VORTEX liquid crystal element and from a Laguerre-Gauss-like beam $LG_{02}'$ and the FWHM of the Gauss beam that has passed through the VORTEX liquid crystal element, where the propagation distance from the VORTEX liquid crystal element to the observation plane is 0.5 times the Rayleigh length, and the angle θ formed between the alignment direction of liquid crystal molecules in the VORTEX liquid crystal element and the polarization direction of the Gauss beam emitted by the light source is 31°.

FIGS. 15A and 15B are diagrams obtained by simulation, each illustrating a relationship between the profile of a composite beam synthesized from a Gauss beam that has passed through the VORTEX liquid crystal element 4 and from a Laguerre-Gauss-like beam $LG_{02}'$ and the FWHM of the Gauss beam that has passed through the VORTEX liquid crystal element 4, where the propagation distance from the VORTEX liquid crystal element 4 to the observation plane is 0.5 times the Rayleigh length, and the angle θ formed between the alignment direction of liquid crystal molecules in the VORTEX liquid crystal element 4 and the polarization direction of the linearly polarized light coming from the light source 1 is 28° or 31°. In each of FIGS. 15A and 15B, the horizontal axis indicates a distance from the optical axis OA, while the vertical axis indicates a ratio of the intensity of the composite beam at a point away from the optical axis OA by the distance r to its maximum intensity. The profile 1501 represents the profile of a Gauss beam that has passed through the VORTEX liquid crystal element 4, while the profiles 1502 and 1503 represent the profiles of composite beams corresponding to angles θ of 28° and 31°, respectively. As indicated in FIGS. 15A and 15B, the ratio of the theoretical intensity of a composite beam to its maximum theoretical intensity is at least 0.72 within the FWHM when the angle θ is at least 28° and not greater than 31°. Therefore, in this case, it is preferable that the angle θ satisfies 28°≤θ≤31°.

Figure 16A:
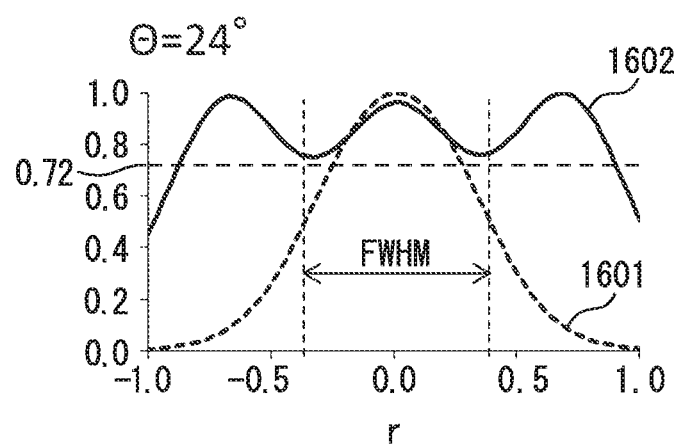
FIG. 16A is a diagram obtained by simulation, illustrating a relationship between the profile of a composite beam synthesized from a Gauss beam that has passed through the VORTEX liquid crystal element and from a Laguerre-Gauss-like beam $LG_{02}'$ and the FWHM of the Gauss beam that has passed through the VORTEX liquid crystal element, where the propagation distance from the VORTEX liquid crystal element to the observation plane is 0.75 times the Rayleigh length, and the angle θ formed between the alignment direction of liquid crystal molecules in the VORTEX liquid crystal element and the polarization direction of the Gauss beam emitted by the light source is 24°.
Figure 16B:
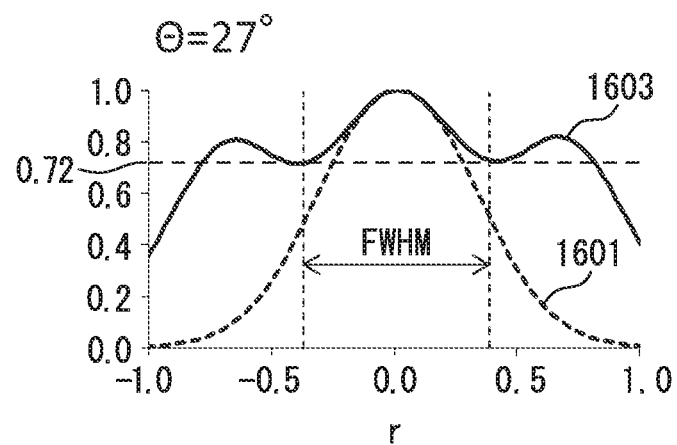
FIG. 16B is a diagram obtained by simulation, illustrating a relationship between the profile of a composite beam synthesized from a Gauss beam that has passed through the VORTEX liquid crystal element and from a Laguerre-Gauss-like beam $LG_{02}'$ and the FWHM of the Gauss beam that has passed through the VORTEX liquid crystal element, where the propagation distance from the VORTEX liquid crystal element to the observation plane is 0.75 times the Rayleigh length, and the angle θ formed between the alignment direction of liquid crystal molecules in the VORTEX liquid crystal element and the polarization direction of the Gauss beam emitted by the light source is 27°.

FIGS. 16A and 16B are diagrams obtained by simulation, each illustrating a relationship between the profile of a composite beam synthesized from a Gauss beam that has passed through the VORTEX liquid crystal element 4 and from a Laguerre-Gauss-like beam $LG_{02}'$ and the FWHM of the Gauss beam that has passed through the VORTEX liquid crystal element 4, where the propagation distance from the VORTEX liquid crystal element 4 to the observation plane is 0.75 times the Rayleigh length, and the angle θ formed between the alignment direction of liquid crystal molecules in the VORTEX liquid crystal element 4 and the polarization direction of the Gauss beam emitted by the light source 1 is 24° or 27°. In each of FIGS. 16A and 16B, the horizontal axis indicates a distance from the optical axis OA, while the vertical axis indicates a ratio of the intensity of the composite beam at a point away from the optical axis OA by the distance r to its maximum intensity. The profile 1601 represents the profile of a Gauss beam that has passed through the VORTEX liquid crystal element 4, while the profiles 1602 and 1603 represent the profiles of composite beams corresponding to angles θ of 24° and 27°, respectively. As indicated in FIGS. 16A and 16B, the ratio of the theoretical intensity of a composite beam to its maximum theoretical intensity is at least 0.72 within the FWHM when the angle θ is at least 24° and not greater than 27°. Therefore, in this case, it is preferable that the angle θ satisfies 24°≤θ≤27°.

Figure 17A:
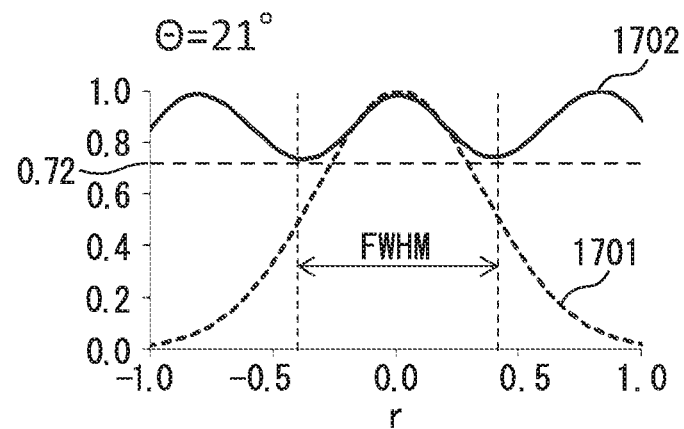
FIG. 17A is a diagram obtained by simulation, illustrating a relationship between the profile of a composite beam synthesized from a Gauss beam that has passed through the VORTEX liquid crystal element and from a Laguerre-Gauss-like beam $LG_{02}'$ and the FWHM of the Gauss beam that has passed through the VORTEX liquid crystal element, where the propagation distance from the VORTEX liquid crystal element to the observation plane is equal to the Rayleigh length, and the angle θ formed between the alignment direction of liquid crystal molecules in the VORTEX liquid crystal element and the polarization direction of the Gauss beam emitted by the light source is 21°.
Figure 17B:
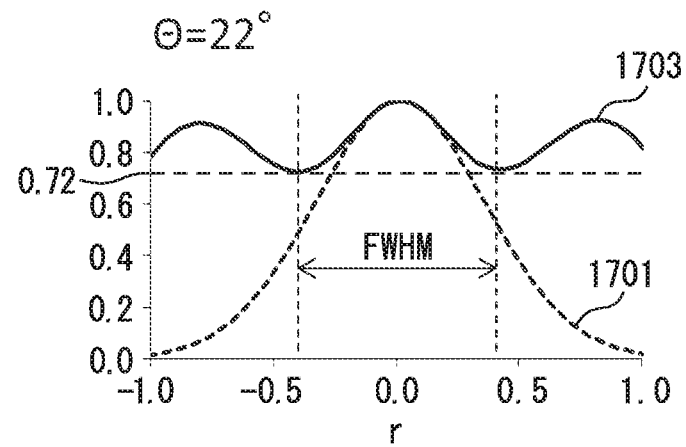
FIG. 17B is a diagram obtained by simulation, illustrating a relationship between the profile of a composite beam synthesized from a Gauss beam that has passed through the VORTEX liquid crystal element and from a Laguerre-Gauss-like beam $LG_{02}'$ and the FWHM of the Gauss beam that has passed through the VORTEX liquid crystal element, where the propagation distance from the VORTEX liquid crystal element to the observation plane is equal to the Rayleigh length, and the angle θ formed between the alignment direction of liquid crystal molecules in the VORTEX liquid crystal element and the polarization direction of the Gauss beam emitted by the light source is 22°.

FIGS. 17A and 17B are diagrams obtained by simulation, each illustrating a relationship between the profile of a composite beam synthesized from a Gauss beam that has passed through the VORTEX liquid crystal element 4 and from a Laguerre-Gauss-like beam $LG_{02}'$ and the FWHM of the Gauss beam that has passed through the VORTEX liquid crystal element 4, where the propagation distance from the VORTEX liquid crystal element 4 to the observation plane is equal to the Rayleigh length, and the angle θ formed between the alignment direction of liquid crystal molecules in the VORTEX liquid crystal element 4 and the polarization direction of the Gauss beam emitted by the light source 1 is 21° or 22°. In each of FIGS. 17A and 17B, the horizontal axis indicates a distance from the optical axis OA, while the vertical axis indicates a ratio of the intensity of the composite beam at a point away from the optical axis OA by the distance r to its maximum intensity. The profile 1701 represents the profile of a Gauss beam that has passed through the VORTEX liquid crystal element 4, while the profiles 1702 and 1703 represent the profiles of composite beams corresponding to angles θ of 21° and 22°, respectively. As indicated in FIGS. 17A and 17B, the ratio of the theoretical intensity of a composite beam to its maximum theoretical intensity is at least 0.72 within the FWHM when the angle θ is at least 21° and not greater than 22°. Therefore, in this case, it is preferable that the angle θ satisfies 21°≤θ≤22°.

Figure 18:
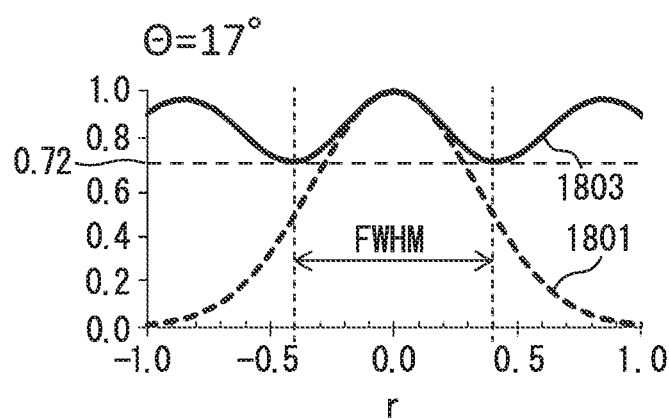
FIG. 18 is a diagram obtained by simulation, illustrating a relationship between the profile of a composite beam synthesized from a Gauss beam that has passed through the VORTEX liquid crystal element and from a Laguerre-Gauss-like beam $LG_{02}'$ and the FWHM of the Gauss beam that has passed through the VORTEX liquid crystal element, where the observation plane is positioned far from the VORTEX liquid crystal element, and the angle θ formed between the alignment direction of liquid crystal molecules in the VORTEX liquid crystal element and the polarization direction of the Gauss beam emitted by the light source is 17°.

FIG. 18 is a diagram obtained by simulation, illustrating a relationship between the profile of a composite beam synthesized from a Gauss beam that has passed through the VORTEX liquid crystal element 4 and from a Laguerre-Gauss-like beam $LG_{02}'$ and the FWHM of the Gauss beam that has passed through the VORTEX liquid crystal element 4, where the observation plane is far enough (i.e., far enough to be regarded as infinity) from the VORTEX liquid crystal element 4, and the angle θ formed between the alignment direction of liquid crystal molecules in the VORTEX liquid crystal element 4 and the polarization direction of the Gauss beam emitted by the light source 1 is 17°. In FIG. 18, the horizontal axis indicates a distance from the optical axis OA, while the vertical axis indicates a ratio of the intensity of the composite beam at a point away from the optical axis OA by the distance r to its maximum intensity. The profile 1801 represents the profile of a Gauss beam that has passed through the VORTEX liquid crystal element 4, while the profile 1802 represents the profile of a composite beam corresponding to an angle θ of 17°. As indicated in FIG. 18, the ratio of the theoretical intensity of a composite beam to its maximum theoretical intensity is at least 0.72 within the FWHM when the angle θ is 17°. Therefore, in this case, it is preferable that the angle θ satisfies θ=17°.

As seen above, a composite beam having a top-hat shape can be obtained by appropriately adjusting the angle θ.

As described above, in the illumination device according to one embodiment of the present invention, the light source that outputs a linearly-polarized Gauss beam and the VORTEX liquid crystal element are placed such that a predetermined angle is formed between the polarization plane of the linearly polarized light and the alignment direction of liquid crystal molecules in the VORTEX liquid crystal element. As a result, the illumination device can form a beam having a top-hat shape, which is a composite beam synthesized from a Gauss beam and a Laguerre-Gauss-like beam obtained along the same optical path by passing the linearly polarized light through the VORTEX liquid crystal element. Since a Gauss beam represents one of propagation modes while a Laguerre-Gauss-like beam has a beam profile similar to a Laguerre-Gauss beam representing one of propagation modes, the composite beam is propagated with its shape relatively maintained. Therefore, the illumination device can provide a composite beam having a top-hat shape, irrespective of the distance from the light source to the observation plane and the distance from the VORTEX liquid crystal element to the observation plane.

The present invention is not limited the foregoing embodiment. According to a modification, the illumination device may use, instead of the VORTEX liquid crystal element, a spiral phase element in which a plurality of phase plates are arranged along the circumference around an optical axis, the phase plates being formed of a uniaxial birefringent crystal, different in thickness, and identical in shape. In this case, optic axes of the individual phase plates are oriented in the same direction. This direction of the optic axes corresponds to the alignment direction of liquid crystal molecules in the foregoing embodiment. The thickness of each phase plate may be determined such that every two adjacent phase plates has the same difference in the amount of phase modulation and that the amount of phase modulation is increased by $2\pi$ or $4\pi$ over one cycle of turning along the circumference.

According to the present modification, a top-hat shaped composite beam can be obtained without applying voltage to the spiral phase element, and thus controls exerted by the controller 9 are simplified.

According to another modification, the illumination devices 11 may further include a support unit 12 (indicated by dotted lines in FIG. 1) that supports either the light source 1 or the VORTEX liquid crystal element 4 rotatably around the optical axis OA. The support unit 12 includes, for example, a cylindrical housing whose center coincides with the optical axis OA, a support member which is attached inside the housing rotatably around the optical axis OA and which supports either the light source 1 or the VORTEX liquid crystal element 4, and a rotating mechanism which rotates the support member by means of a stepping motor via a drive mechanism such as a gear. In this case, the memory 10 stores a table for a modulation component to be turned into a Laguerre-Gauss-like beam $LG_{01}'$, the table indicating a relationship between a distance from the VORTEX liquid crystal element 4 to the observation plane and a first angle formed between the polarization plane of linearly polarized light emitted by the light source 1 and the alignment direction of the VORTEX liquid crystal element 4, as well as storing a table for a modulation component to be turned into a Laguerre-Gauss-like beam $LG_{02}'$, the table indicating a relationship between a distance from the VORTEX liquid crystal element 4 to the observation plane and a second angle formed between the polarization plane of linearly polarized light emitted by the light source 1 and the alignment direction of the VORTEX liquid crystal element 4. Each of the first and second angles falls within a range of angles, ensuring that the composite beam has an intensity of at least 0.8 times its maximum intensity within the full width at half maximum of a Gauss beam that has passed through the VORTEX liquid crystal element 4. When the modulation component is to be turned into a Laguerre-Gauss-like beam $LG_{01}'$, the controller 9 may refer to the distance from the VORTEX liquid crystal element to the observation plane and refer to the first table to control the stepping motor in the support unit 12 so that the aforementioned certain angle $\theta$ is adjusted to the first angle. Likewise, when the modulation component is to be turned into a Laguerre-Gauss-like beam $LG_{02}'$, the controller 9 may refer to the distance from the VORTEX liquid crystal element to the observation plane and refer to the second table to control the stepping motor in the support unit 12 so that the aforementioned certain angle $\theta$ is adjusted to the second angle. Distances from the VORTEX liquid crystal element to the observation plane may be preset and stored in the memory 10 in accordance with, for example, the specifications of an apparatus incorporating the illumination device 11. Alternatively, distances from the VORTEX liquid crystal element to the observation plane may be input into the controller 9 via a user interface.

Alternatively, the controller 9 may control the stepping motor in the support unit 12 so that the certain angle $\theta$ is adjusted to 0°. In this case, all the illumination light passing through the VORTEX liquid crystal element 4 is modulated into Laguerre-Gauss-like beams. Likewise, the controller 9 may control the stepping motor in the support unit 12 so that the certain angle $\theta$ is adjusted to 90°, or may allow the amount of phase modulation to be zero over one cycle of turning along the circumference; in other words, a constant voltage may be applied to the whole liquid crystal layer in the VORTEX liquid crystal element 4. In this case, the illumination light passing through the VORTEX liquid crystal element 4 undergoes no modulation, and thus the beams remain Gauss beams after passing through the VORTEX liquid crystal element 4.

According to still another modification, the illumination light emitted by the light source 1 may be circularly polarized light or elliptically polarized light. As with linearly polarized light, the circularly polarized light and the elliptically polarized light each include a first polarized light component and a second polarized light component orthogonal to each other. When the illumination light is circularly polarized light, the light includes a polarized light component (a first polarized light component, for example) parallel to the alignment direction of liquid crystal molecules in the VORTEX liquid crystal element 4 and another polarized light component orthogonal to the alignment direction, in which case both of the polarized light components are the same in size. Thus, the composite beam obtained by passing the illumination light, which is circularly polarized light, through the VORTEX liquid crystal element 4 has a top-hat shaped profile that is almost equal to that of the composite beam obtained by passing linearly polarized light through the VORTEX liquid crystal element 4, where the linearly polarized light has the polarization plane forming an angle of 45° with the alignment direction of liquid crystal molecules in the VORTEX liquid crystal element 4. In this case, the profile of the resulting composite beam exhibits a good rotation symmetry about the optical axis. As a result, the microscope device 100 equipped with the illumination device 11 can be free from directional dependence of resolution.

When the illumination light is elliptically polarized light, the composite beam obtained by passing the illumination light through the VORTEX liquid crystal element 4 represents a beam as if the beam is further synthesized from the composite beam obtained by passing the illumination light, which is circularly polarized light, through the VORTEX liquid crystal element 4, and from the composite beam obtained by passing the illumination light, which is linearly polarized light, through the VORTEX liquid crystal element 4. Accordingly, the profile of the obtained composite beam changes with the angle $\theta$, which is formed between the ellipse orientation axis (major axis) of the elliptically polarized light and the alignment direction of liquid crystal molecules in the VORTEX liquid crystal element 4, as in the case with the angle $\theta$ formed between the polarization plane of the illumination light, which is linearly polarized light, and the alignment direction of liquid crystal molecules in the VORTEX liquid crystal element 4. Therefore, as in the foregoing modification, the controller 9 may control the stepping motor in the support unit 12 so that the angle $\theta$ is changed with the distance from the VORTEX liquid crystal element 4 to the observation plane. Note that, however, the profile of the composite beam changes with the angle θ to a smaller extent as the ellipticity of the elliptically polarized light is closer to 1. A plane that includes the major axis of elliptically polarized light is herein referred to as the polarization plane of the elliptically polarized light, like the polarization plane of linearly polarized light.

As in the case where the illumination light is linearly polarized light, when the illumination light is either circularly or elliptically polarized light, the illumination device 11 can change the profile shape of the obtained composite beam, owing to the controller 9 adjusting the voltage applied to the VORTEX liquid crystal element 4, to switch the amount, between 2π and 4π, of phase modulation provided to the illumination light passing through the VORTEX liquid crystal element 4 over one cycle of turning along the circumference around the optical axis OA.

The illumination device according to any of the foregoing embodiments and modifications may be combined with an optical system for lighting in a microscope, where optical systems for lighting and observation are independently provided. Alternatively, the illumination device according to any of the foregoing embodiments and modifications may be used for a device other than microscopes, such as a laser machining device.

Figure 19:
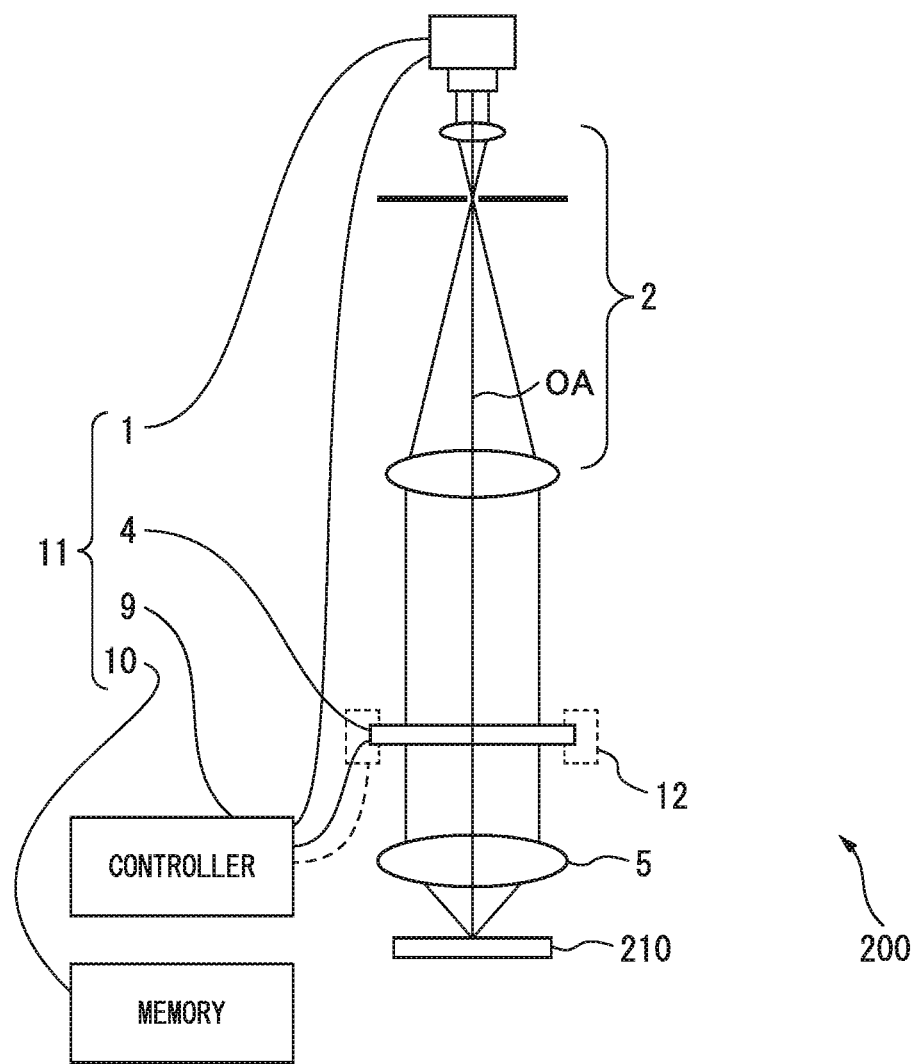
FIG. 19 is a schematic configuration diagram of a machining device that includes an illumination device according to another embodiment of the present invention.

FIG. 19 is a schematic configuration diagram of a laser machining device that includes the illumination device according to any of the foregoing embodiments or modifications. As illustrated in FIG. 19, the laser machining device 200 includes a light source 1, a collimate optical system 2, a VORTEX liquid crystal element 4, an objective lens 5, a controller 9, and a memory 10. Among these elements, the light source 1, the VORTEX liquid crystal element 4, the controller 9, and the memory 10 are included in the illumination device 11. As in the foregoing modification, the illumination device 11 may further include a support unit 12 (indicated by dotted lines in FIG. 19) that supports either the light source 1 or the VORTEX liquid crystal element 4 rotatably around the optical axis OA. The laser machining device 200 may include, on an optical path, any of various correction optical systems such as a spherical aberration correction optical system. The laser machining device 200 may further include a movable stage, such as an XY stage, on which a workpiece 210 is placed.

In FIG. 19, individual elements are given reference numbers identical to those given to the corresponding elements of the microscope device 100 illustrated in FIG. 1.

As in the foregoing embodiments or modifications, the light source 1 emits illumination light that has a Gaussian beam profile. The illumination light may be linearly polarized light having a polarization plane that forms an angle greater than 0° and less than 90° with the alignment direction of liquid crystal molecules in the VORTEX liquid crystal element 4, or may be circularly polarized or elliptically polarized light, so that the illumination light includes a first polarized light component and a second polarized light component orthogonal to each other.

As in the foregoing embodiments or modifications, the light source 1 includes, for example, a semiconductor laser. Alternatively, the light source 1 may include a gas laser such as an argon-ion laser or a solid-state laser such as a YAG laser. The light source 1 may include a plurality of light emitting elements that emit light beams of different wavelengths from one another. In this case, the light source 1 causes any one of the light emitting elements to emit illumination light in accordance with a control signal from the controller 9.

The collimate optical system 2 is placed between the light source 1 and the VORTEX liquid crystal element 4 so that the light source 1 is positioned at the front focal point of the collimate optical system 2. The collimate optical system 2 turns the illumination light emitted from the light source 1 into a parallel beam of light. The parallel beam of illumination light is directed toward the VORTEX liquid crystal element 4.

The VORTEX liquid crystal element 4 may be the VORTEX liquid crystal element according to any of the foregoing embodiments or modifications, and is placed, for example, between the collimate optical system 2 and the objective lens 5 such that its center coincides with the optical axis OA that is defined by the collimate optical system 2 and the objective lens 5. When the illumination light passes through the VORTEX liquid crystal element 4, the VORTEX liquid crystal element 4 generates a modulation component that has a Laguerre-Gauss-like beam profile, and generates a top-hat beam, which is a composite beam synthesized from a non-modulation component and the modulation component.

The objective lens 5 focuses top-hat beams outgoing from the VORTEX liquid crystal element 4 on a work surface provided on the workpiece 210. With the top-hat beams focused on the work surface, the workpiece 210 may be drilled, for example.

The controller 9 includes, for example, one or more processors and an interface circuit used for connecting the controller 9 to the individual elements of the laser machining device 200. The controller 9 controls the light source 1 and the VORTEX liquid crystal element 4. The controller 9 supplies a certain amount of electric power to the light source 1 to cause the light source 1 to emit illumination light. When the light source 1 includes a plurality of light emitting elements, the controller 9 sends the light source 1 a control signal indicating that any one of the light emitting elements is to emit illumination light in accordance with, for example, a user operation performed through a user interface. If the laser machining device 200 includes a movable stage, the controller 9 may control the movable stage to move the workpiece 21 placed on the movable state. This moves the workpiece 210 relative to the light focusing spot of a top-hat beam, and thus the laser machining device 200 is allowed to machine other points of the workpiece 210.

Furthermore, as in the foregoing embodiments or modifications, the controller 9 includes a drive circuit, through which the controller 9 adjusts the voltage applied to the VORTEX liquid crystal element 4. In this way, the controller 9 controls the VORTEX liquid crystal element 4 so as to form a top-hat beam. During the operation, the controller 9 can switch the modulation component to be combined with the non-modulation component, which is a Gauss beam, between a Laguerre-Gauss-like beam $LG_{01}'$ and a Laguerre-Gauss-like beam $LG_{02}'$, by adjusting the voltage applied to the VORTEX liquid crystal element 4 over one cycle of turning along the circumference around the optical axis OA, as in the foregoing embodiments or modifications. In this way, the controller 9 can adjust the size of the light-focusing spot of a top-hat beam.

In addition, if the illumination device 11 includes the support unit 12, the controller 9 may control the stepping motor in the support unit 12 so as to adjust the angle θ formed between the polarization plane of the illumination light (or the major axis of elliptically polarized light, if applicable) and the alignment direction of liquid crystal molecules in the VORTEX liquid crystal element 4, as in the foregoing modifications. As a result, the illumination device 11 can adjust the orientations of the light source 1 and the VORTEX liquid crystal element 4, so as to obtain an angle θ appropriate for the distance from the VORTEX liquid crystal element 4 to the work surface or for the amount of phase modulation over one cycle of turning around the optical axis.

The memory 10 includes, for example, a volatile readable and writable semiconductor memory circuit or a nonvolatile read-only memory circuit. The memory 10 may further include a magnetic or optical recording medium and a device for accessing the medium. The memory 10 is connected to the controller 9 and stores data to be used by the controller 9 for controlling the light source 1 and the VORTEX liquid crystal element 4.

When the illumination device 11 is included in the laser machining device 200, the illumination device 11 may also use, instead of the VORTEX liquid crystal element, a spiral phase element in which a plurality of phase plates are arranged along the circumference around an optical axis, the phase plates being formed of a uniaxial birefringent crystal, different in thickness, and identical in shape.

As is evident from the above description, those skilled in the art can make various modifications to the embodiments without departing from the scope and spirit of the present invention.

REFERENCE SIGNS LIST

100 Microscope device
1 Light source
2 Collimate optical system
3 Beam splitter
4 VORTEX liquid crystal element
5 Objective lens
6 Confocal optical system
7 Mask plate
7a Confocal pinhole
8 Light receiving element
9 Controller
10 Memory
11 Illumination device
12 Support unit
110 Sample
40 Liquid crystal layer
41, 42 Transparent substrate
43, 44 Transparent electrode
43-1 to 43-$m$ Partial electrode
45, 46 Alignment film
47 Liquid crystal molecule
48 Sealing member
200 Laser machining device

The invention claimed is:

1. An illumination device comprising:
a light source which emits polarized light that has a Gaussian beam profile and that includes a first polarized light component and a second polarized light component orthogonal to each other; and
a spiral phase element which provides an amount of phase modulation to the first polarized light component of the polarized light passing through the spiral phase element to turn the beam profile of the first polarized light component into a Laguerre-Gauss-like beam profile, where the amount of the phase modulation is increased by a predetermined amount along a circumference direction around an optical axis, and which forms a composite beam that has a top-hat-shaped beam profile and that is synthesized from the second polarized light component of the polarized light passing through the spiral phase element and from the first polarized light component having the Laguerre-Gauss-like beam profile.

2. The illumination device according to claim 1, wherein the spiral phase element comprises:
a liquid crystal layer which includes liquid crystal molecules aligned along a first direction;
a first transparent electrode which is disposed on one side of the liquid crystal layer along the optical axis; and
a second transparent electrode which is disposed on another side of the liquid crystal layer along the optical axis, and which includes a plurality of partial electrodes arranged along the circumferential direction around the optical axis,
wherein a voltage applied to a partial region of the liquid crystal layer between each of the plurality of the partial electrodes and the first transparent electrode is controlled such that the amount of phase modulation is increased by the predetermined amount between the partial regions adjacent to each other, whereby the beam profile of the first polarized light component is turned into the Laguerre-Gauss-like beam profile, and
wherein the polarized light is linearly polarized light which has a polarization plane forming a predetermined angle greater than 0☐ and less than 90☐ with the first direction, the first polarized light component is a component parallel to the first direction, and the second polarized light component is a component orthogonal to the first direction.

3. The illumination device according to claim 2, wherein the predetermined angle falls within an angular range in which the composite beam has an intensity of at least 0.8 times a maximum intensity of the composite beam within a range of a full width at half maximum of the second polarized light component.

4. The illumination device according to claim 2, further comprising:
a support unit which supports either one of the spiral phase element and the light source rotatably around the optical axis;
a memory which stores a table representing a correspondence relationship between a distance from the spiral phase element to a plane irradiated with the composite beam and an angle formed between the polarization plane of the polarized light and the first direction; and
a controller which refers to the table and controls the support unit so as to rotate the either one of the spiral phase element and the light source so that an angle formed between the polarization plane of the polarized light and the first direction corresponds to the distance.

5. The illumination device according to claim 2, further comprising:
a memory which stores first voltages to be applied between the plurality of the individual partial electrodes and the first transparent electrode when phase modulation provided by the spiral phase element to the first polarized light component over one cycle of turning along the circumference direction is increased by an amount equivalent to a wavelength of the polarized light, and which stores second voltages to be applied between the plurality of the individual partial electrodes and the first transparent electrode when phase modulation provided by the spiral phase element to the first polarized light component over one cycle of turning along the circumference direction is increased by an amount equivalent to twice the wavelength of the polarized light; and a controller which sets a voltage to be applied between each of the plurality of the partial electrodes and the first transparent electrode in accordance with the first voltages when phase modulation provided by the spiral phase element to the first polarized light component is increased over one cycle of turning along the circumference direction by an amount equivalent to the wavelength of the polarized light, and which sets a voltage to be applied between each of the plurality of the partial electrodes and the first transparent electrode in accordance with the second voltages when phase modulation provided by the spiral phase element to the first polarized light component is increased over one cycle of turning along the circumference direction by an amount equivalent to twice the wavelength of the polarized light.

6. The illumination device according to claim 5, further comprising:

a support unit which supports either one of the spiral phase element and the light source rotatably around the optical axis, wherein the memory further stores a first angle to be formed between the polarization plane of the polarized light and the first direction when phase modulation provided by the spiral phase element to the first polarized light component over one cycle of turning along the circumference direction is increased by an amount equivalent to the wavelength of the polarized light, and further stores a second angle to be formed between the polarization plane of the polarized light and the first direction when phase modulation provided by the spiral phase element to the first polarized light component over one cycle of turning along the circumference direction is increased by an amount equivalent to twice the wavelength of the polarized light, and wherein the controller causes the support unit to rotate either one of the spiral phase element and the light source so that the predetermined angle is equal to the first angle when phase modulation provided by the spiral phase element to the first polarized light component over one cycle of turning along the circumference direction is increased by an amount equivalent to the wavelength of the polarized light, and causes the support unit to rotate either one of the spiral phase element and the light source so that the predetermined angle is equal to the second angle when phase modulation provided by the spiral phase element to the first polarized light component over one cycle of turning along the circumference direction is increased by an amount equivalent to twice the wavelength of the polarized light.

7. The illumination device according to claim 1, wherein the polarized light is circularly polarized light or elliptically polarized light.

8. The illumination device according to claim 7, wherein the spiral phase element comprises:

a liquid crystal layer which includes liquid crystal molecules aligned along a first direction that is parallel to the first polarized light component;

a first transparent electrode which is disposed on one side of the liquid crystal layer along the optical axis; and a second transparent electrode which is disposed on another side of the liquid crystal layer along the optical axis, and which includes a plurality of partial electrodes arranged along the circumferential direction around the optical axis, wherein a voltage applied to a partial region of the liquid crystal layer between each of the plurality of the partial electrodes and the first transparent electrode is controlled such that the amount of phase modulation is increased by the predetermined amount between the partial regions adjacent to each other, whereby the beam profile of the first polarized light component is turned into a Laguerre-Gauss-like beam profile.

9. The illumination device according to claim 8, wherein the polarized light is elliptically polarized light, the illumination device further comprising:

a support unit which supports either one of the spiral phase element and the light source rotatably around the optical axis;

a memory which stores a table representing a correspondence relationship between a distance from the spiral phase element to a plane irradiated with the composite beam and an angle formed between a major axis of the polarized light and the first direction; and a controller which refers to the table and controls the support unit so as to rotate the either one of the spiral phase element and the light source so that an angle formed between the major axis of the polarized light and the first direction corresponds to the distance.

10. A method for generating illumination light in an illumination device which comprises:

a light source which emits illumination light that has a Gaussian beam profile, that is linearly polarized light or elliptically polarized light, and that has a predetermined polarization plane; and a spiral phase element which provides an amount of phase modulation, the amount being increased by a predetermined amount along a circumference direction around an optical axis, to a first polarized light component of the illumination light passing through the spiral phase element, the first polarized light component having a first direction on a plane orthogonal to the optical axis, to turn the beam profile of the first polarized light component into a Laguerre-Gauss-like beam profile, and which forms a composite beam that has a top-hat-shaped beam profile and that is synthesized from a second polarized light component of the illumination light passing through the spiral phase element, the second polarized light component being orthogonal to the first polarized light component, and from the first polarized light component having the Laguerre-Gauss-like beam profile, wherein the spiral phase element comprises:

a liquid crystal layer which includes liquid crystal molecules aligned along the first direction;

a first transparent electrode which is disposed on one side of the liquid crystal layer along the optical axis; and a second transparent electrode which is disposed on another side of the liquid crystal layer along the optical axis, and which includes a plurality of partial electrodes arranged along the circumferential direction around the optical axis, the method comprising the steps of:

applying a voltage to a partial region of the liquid crystal layer between each of the plurality of the partial electrodes and the first transparent electrode so that the amount of phase modulation is increased by the predetermined amount between the partial regions adjacent to each other to turn the beam profile of the first component into a Laguerre-Gauss-like beam profile; and referring to a table representing a correspondence relationship between a distance from the spiral phase element to a plane irradiated with the composite beam and an angle formed between the predetermined polarization plane and the first direction, to rotate either one of the light source and the spiral phase element around the optical axis so that an angle formed between the predetermined polarization plane and the first direction corresponds to the distance.

11. A method for generating illumination light in an illumination device which comprises:

a light source which emits polarized light that has a Gaussian beam profile and that includes a first polarized light component and a second polarized light component orthogonal to each other; and a spiral phase element which provides an amount of phase modulation to the first polarized light component of the polarized light passing through the spiral phase element to turn the beam profile of the first polarized light component into a Laguerre-Gauss-like beam profile, where the amount of the phase modulation is increased by a predetermined amount along a circumference direction around an optical axis, and which forms a composite beam that has a top-hat-shaped beam profile and that is synthesized from the second polarized light component of the polarized light passing through the spiral phase element and from the first polarized light component having the Laguerre-Gauss-like beam profile, wherein the spiral phase element comprises:

a liquid crystal layer which includes liquid crystal molecules aligned along a first direction that is parallel to the first polarized light component;

a first transparent electrode which is disposed on one side of the liquid crystal layer along the optical axis; and a second transparent electrode which is disposed on another side of the liquid crystal layer along the optical axis, and which includes a plurality of partial electrodes arranged along the circumferential direction around the optical axis, the method comprising the steps of:

setting a voltage to be applied between each of the plurality of the partial electrodes and the first transparent electrode in accordance with first voltages when phase modulation provided by the spiral phase element to the first polarized light component is increased over one cycle of turning along the circumference direction by an amount equivalent to a wavelength of the polarized light, while setting a voltage to be applied between each of the plurality of the partial electrodes and the first transparent electrode in accordance with second voltages when phase modulation provided by the spiral phase element to the first polarized light component is increased over one cycle of turning along the circumference direction by an amount equivalent to twice the wavelength of the polarized light; and applying the set voltage to a partial region of the liquid crystal layer between each of the plurality of the partial electrodes and the first transparent electrode to turn the beam profile of the first polarized light component into a Laguerre-Gauss-like beam profile.

* * * * *